US012186454B2

(12) United States Patent
Machluf et al.

(10) Patent No.: US 12,186,454 B2
(45) Date of Patent: Jan. 7, 2025

(54) SCAFFOLDS FABRICATED FROM ELECTROSPUN DECELLULARIZED EXTRACELLULAR MATRIX

(71) Applicant: Technion Research & Development Foundation Limited, Haifa (IL)

(72) Inventors: Marcelle Machluf, Haifa (IL); Eyal Zussman, Haifa (IL); Limor Baruch, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 18/100,000

(22) Filed: Jan. 23, 2023

(65) Prior Publication Data

US 2023/0158208 A1    May 25, 2023

Related U.S. Application Data

(62) Division of application No. 16/092,787, filed as application No. PCT/IL2017/050428 on Apr. 6, 2017, now abandoned.

(30) Foreign Application Priority Data

Apr. 12, 2016 (IL) .......................................... 245059

(51) Int. Cl.

| A61L 27/38 | (2006.01) |
| A61K 35/28 | (2015.01) |
| A61L 27/18 | (2006.01) |
| A61L 27/24 | (2006.01) |
| A61L 27/36 | (2006.01) |
| A61P 3/10 | (2006.01) |
| A61P 9/00 | (2006.01) |

(52) U.S. Cl.
CPC .......... *A61L 27/3804* (2013.01); *A61K 35/28* (2013.01); *A61L 27/18* (2013.01); *A61L 27/24* (2013.01); *A61L 27/3633* (2013.01); *A61L 27/38* (2013.01); *A61P 3/10* (2018.01); *A61P 9/00* (2018.01)

(58) Field of Classification Search
CPC ...... A61L 24/3804; A61L 27/18; A61L 27/24; A61L 27/3633; A61L 27/38; A61P 9/00; A61P 3/10; A61K 35/28; C08L 71/02
USPC ....................................................... 424/93.7
See application file for complete search history.

(56) References Cited

U.S. PATENT DOCUMENTS

| 2006/0253192 A1 | 11/2006 | Atala et al. |
| 2011/0287082 A1 | 11/2011 | Smith et al. |
| 2011/0295028 A1* | 12/2011 | Cherinko ................. C11B 3/02 554/175 |
| 2013/0251687 A1 | 9/2013 | Christman et al. |
| 2013/0253663 A1 | 9/2013 | Amoroso et al. |
| 2016/0000834 A1 | 1/2016 | Kinsey et al. |
| 2016/0166730 A1 | 6/2016 | Matheny |
| 2019/0142998 A1 | 5/2019 | Machluf et al. |

FOREIGN PATENT DOCUMENTS

| WO | WO 2006/138718 | 12/2006 |
| WO | WO 2010/041944 | 4/2010 |
| WO | WO 2012/024390 | 2/2013 |
| WO | WO 2013/119873 | 8/2013 |
| WO | WO 2014/160463 | 10/2014 |
| WO | WO 2017/179042 | 10/2017 |

OTHER PUBLICATIONS

Wikipedia, Polycaprolactone, Accessed Sep. 24, 2023, Available online at: https://en.wikipedia.org/wiki/Polycaprolactone.*
Office Action Dated Mar. 9, 2023 From the Israel Patent Office Re. Application No. 262318 and Its Translation Into English. (6 Pages).
Advisory Action Dated May 11, 2022 From the US Patent and Trademark Office Re. U.S. Appl. No. 16/092,787. (3 Pages).
Communication Pursuant to Article 94(3) EPC Dated Dec. 7, 2021 From the European Patent Office Re. Application No. 17782049.5. (9 Pages).
Examination Report Under Sections 12 & 13 of the Patents Act, 1970 and the Patents Rules, 2003 Dated Aug. 31, 2022 From the Govenment of India, Intellectual Property India, Patents, Designs, Trade Marks, Geographical Indications, the Patent Office Re. Application No. 201827041590. (8 Pages).
Final Official Action Dated Feb. 10, 2022 from US Patent and Trademark Office Re. U.S. Appl. No. 16/092,787. (10 pages).
International Preliminary Report on Patentability Dated Oct. 25, 2018 From the International Bureau of WIPO Re. Application No. PCT/IL2017/050428. (9 Pages).
International Search Report and the Written Opinion Dated Jul. 19, 2017 From the International Searching Authority Re. Application No. PCT/IL2017/050428. (13 Pages).
Notification of Office Action and Search Report Dated May 20, 2021 From the State Intellectual Property Office of the People's Republic of China Re. Application No. 201780036212.7 and Its Translation of Office Action Into English. (29 Pages).
Notification of Office Action Dated Dec. 17, 2021 From the State Intellectual Property Office of the People's Republic of China Re. Application No. 201780036212.7 and Its Translation of Office Action Into English. (17 Pages).
Notification of Office Action Dated May 24, 2022 From the State Intellectual Property Office of the People's Republic of China Re. Application No. 201780036212.7 and Its Translation of Office Action Into English. (17 Pages).
Office Action and Search Report Dated Jul. 17, 2017 From the Israel Patent Office Re. Application No. 245059. (14 Pages).
Office Action Dated Oct. 20, 2021 From the Israel Patent Office Re. Application No. 262318 and Its Translation Into English. (8 Pages).

(Continued)

*Primary Examiner* — Jennifer M. H. Tichy

(57) ABSTRACT

A scaffold comprising electrospun decellularized ECM of an organ, wherein the decellularized ECM has a similar protein composition to native ECM of the organ. Methods of generating same are also disclosed as well as uses of same.

13 Claims, 27 Drawing Sheets

Specification includes a Sequence Listing.

(56) References Cited

OTHER PUBLICATIONS

Official Action Dated Sep. 1, 2022 from US Patent and Trademark Office Re. U.S. Appl. No. 16/092,787. (9 pages).
Official Action Dated Jun. 18, 2021 from the US Patent and Trademark Office Re. U.S. Appl. No. 16/092,787. (13 pages).
Restriction Official Action Dated Feb. 5, 2021 From the US Patent and Trademark Office Re. U.S. Appl. No. 16/092,787. (8 Pages).
Supplementary European Search Report and the European Search Opinion Dated Dec. 9, 2019 From the European Patent Office Re. Application No. 17782049.5. (15 Pages).
Baker et al. "The Potential to Improve Cell Infiltration in Composite Fiber-Aligned Electrospun Scaffolds by the Selective Removal of Sacrificial Fibers", Biomaterials, XP022526907, 29(15): 2348-2358, Available Online Mar. 3, 2008.
Buerck et al. "Resemblance of Electrospun Collagen Nanofibers to Their Native Structure", Langmuir, XP055644391, 29(5): 1562-1572, Published Online Dec. 22, 2012.
Cescon et al. "Collagen VI at a Glance", Journal of Cell Science, XP055644217, 128(19): 3525-3531, Published Online Sep. 16, 2015.
Francis et al. "Electrospinning Adipose Tissue-Derived Extracellular Matrix for Adipose Stem Cell Culture", Journal of Biomedical Meterials Research, Part A, XP055186860, 100(7): 1716-1724, Published Online Mar. 23, 2012.
Gibson et al. "Tissue Extracellular Matrix Nanoparticle Presentation in Electrospun Nanofibers", BioMed Research International, XP055347054, 2014(Art. ID 469120): 1-13, Published Online May 29, 2014.
Goh et al. "Perfusion-Decellularized Pancreas as a Natural 3D Scaffold for Pancreatic Tissue and Whole Organ Engineering", Biomaterials, XP028573430, 43(28): 6760-6772, Available Online Jun. 17, 2013.
Hong et al. "An Elastomeric Patch Electrospun From a Blended Solution of Dermal Extracellular Matrix and Biodegradable Polyurethane for Rat Abdominal Wall Repair", Tissue Engineering, Part C: Methods, XP055433831, 18(2): 122-132, Published Online Nov. 11, 2011. Abstract, Material and Methods, Fig.7.
Ma et al. "Electrospun Sodium Alginate/Poly(Ethylene Oxide) Core-Shell Nanofibers Scaffolds Potential for Tissue Engineering Applications", Carbohydrate Polymers, 87(1): 737-743, Available Online Aug. 25, 2011. Abstract.
Shafy et al. "Development of Cardiac Support Bioprotheses for Ventricular Restoration and Myocardial Regeneration", European Journal of Cardio-Thoracic Surgery, 43(6): 1211-1219, Published Online Aug. 31, 2012. p. 1214, Section Titled 'Echocardiography'm p. 1215, Section Titled 'Histological Results'.
Skotak et al. "Improved Cellular Infiltration Into Nanofibrous Electrospun Cross-Linked Gelatin Scaffolds Templated With Micrometer-Sized Polyethylene Glycol Fibers", Biomedical Materials, XP055643940, 6(5): 055012-1-055012-10, Published Online Sep. 19, 2011.
Stankus et al. "Hybrid Nanofibrous Scaffolds From Electrospunning of a Synthetic Biodegradable Elastomer and Urinary Bladder Matrix", Journal of Biomaterials Science, Polymer Edition, XP055433828, 19(5): 635-652, May 1, 2008. Materials and Methods.
Wu et al. "3D Culture of MIN-6 Cells on Decellularized Pancreatic Scaffold: In Vitro and In Vivo Study", BioMed Research International, 2015(Art.ID 432645): 1-8, Published Online Nov. 24, 2015.

\* cited by examiner

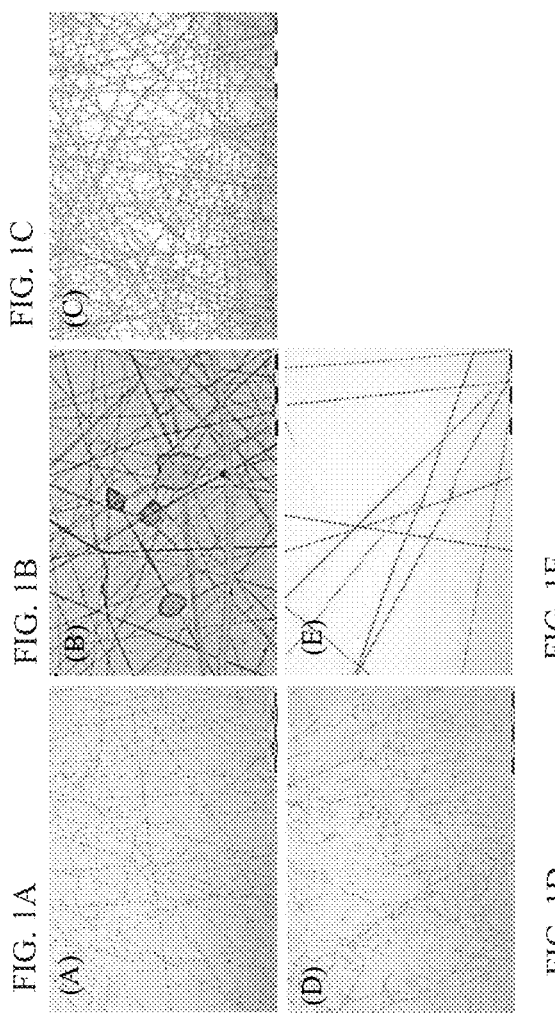

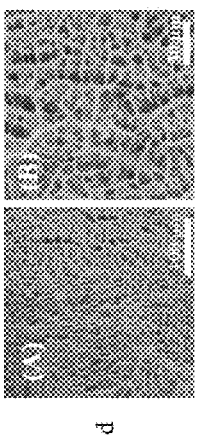
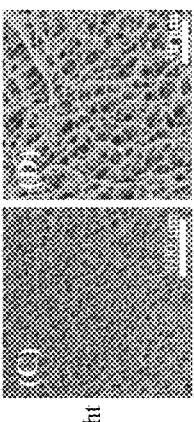
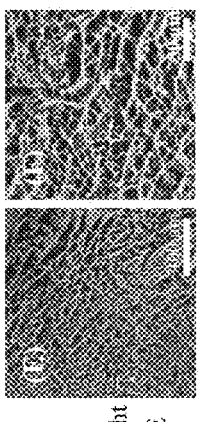
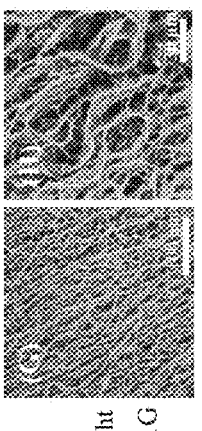
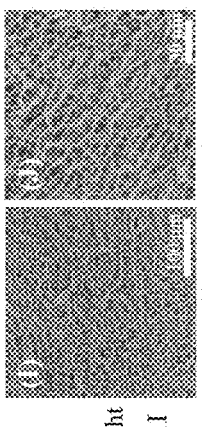
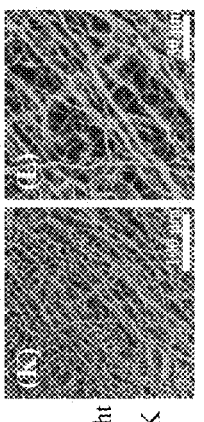
FIG. 11A None (Decellularized ECM)
FIG. 11B
FIG. 11C 37 °C for 1 hr + 37 °C overnight
FIG. 11D
FIG. 11E 24 °C for 1 hr + 24 °C overnight
FIG. 11F
FIG. 11G 4 °C for 1 hr + 4 °C overnight
FIG. 11H
FIG. 11I 24 °C for 1 hr + 37 °C overnight
FIG. 11J
FIG. 11K 4 °C for 1 hr + 37 °C overnight
FIG. 11L

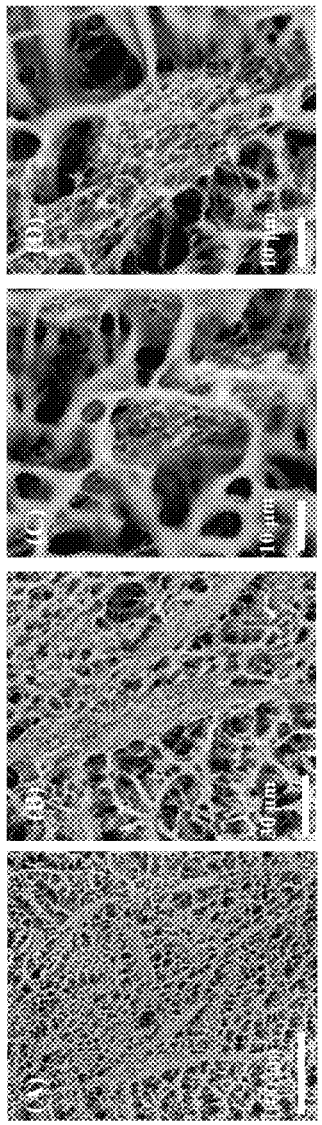

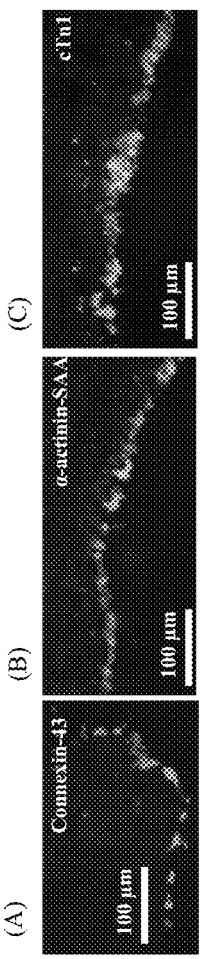

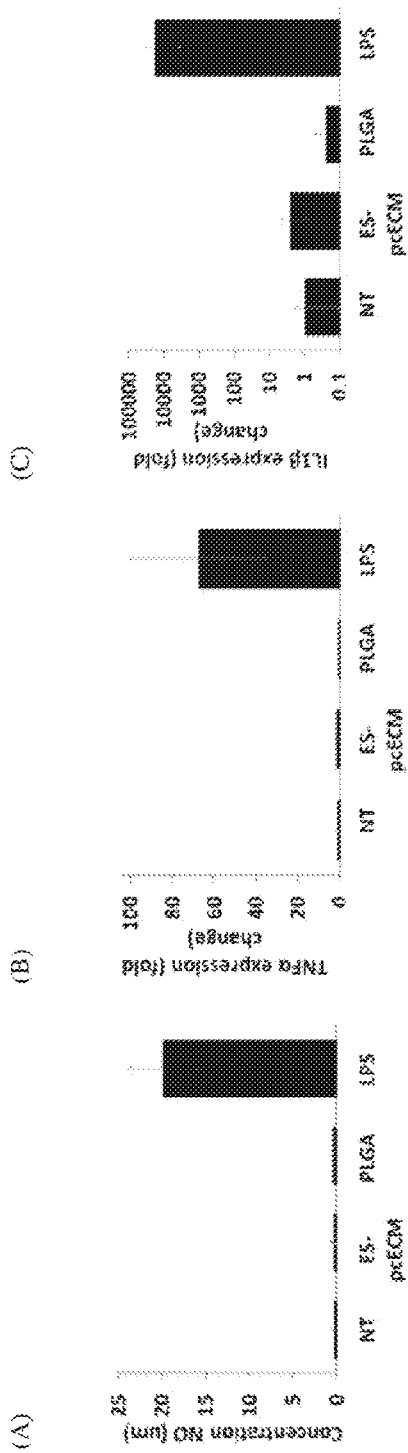
FIGs. 25A-C

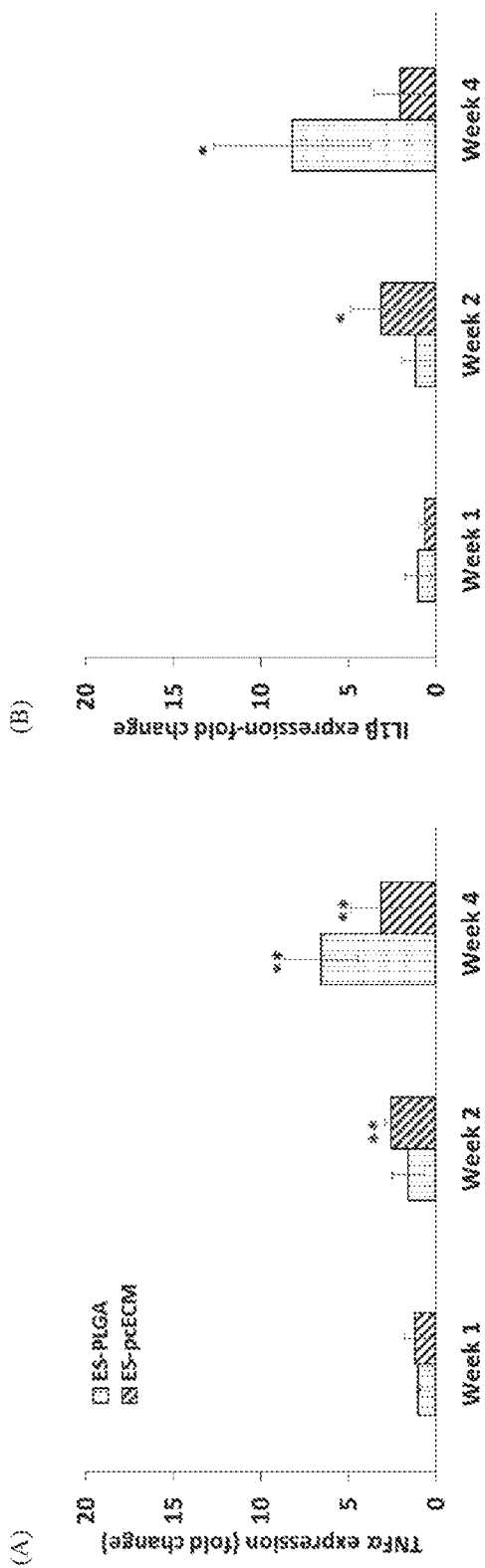
FIGs. 26A-B

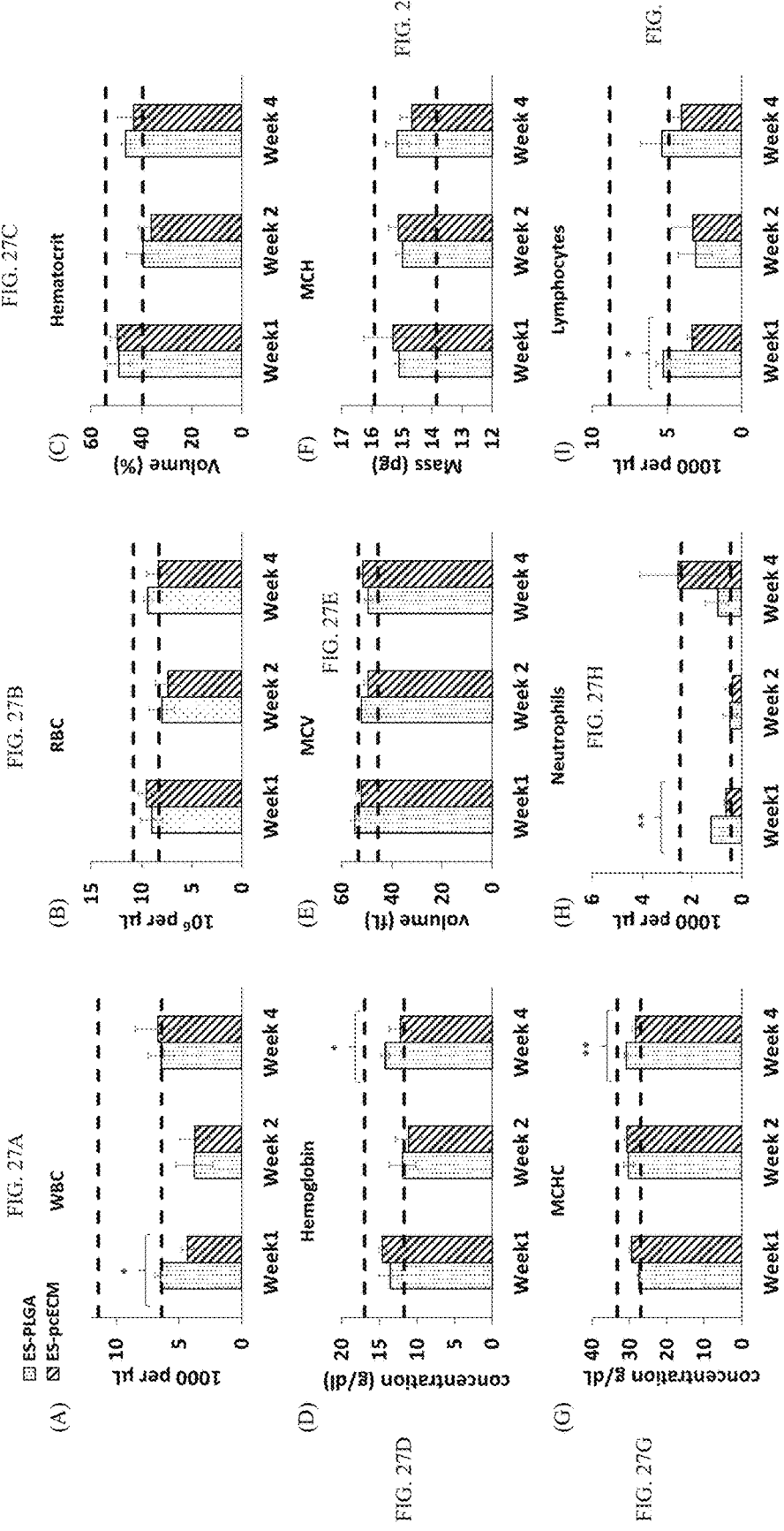

SEQUENCE LISTING

```
Sequence total quantity: 14
SEQ ID NO: 1              moltype = DNA  length = 20
FEATURE                   Location/Qualifiers
misc_feature              1..20
                          note = Single strand DNA oligonucleotide
source                    1..20
                          mol_type = other DNA
                          organism = synthetic construct
SEQUENCE: 1
gcctccctct catcagttct                                                     20

SEQ ID NO: 2              moltype = DNA  length = 20
FEATURE                   Location/Qualifiers
misc_feature              1..20
                          note = Single strand DNA oligonucleotide
source                    1..20
                          mol_type = other DNA
                          organism = synthetic construct
SEQUENCE: 2
tggtggtttg ctacgacgtg                                                     20

SEQ ID NO: 3              moltype = DNA  length = 20
FEATURE                   Location/Qualifiers
misc_feature              1..20
                          note = Single strand DNA oligonucleotide
source                    1..20
                          mol_type = other DNA
                          organism = synthetic construct
SEQUENCE: 3
aggatgagga catgagcacc                                                     20

SEQ ID NO: 4              moltype = DNA  length = 20
FEATURE                   Location/Qualifiers
misc_feature              1..20
                          note = Single strand DNA oligonucleotide
source                    1..20
                          mol_type = other DNA
                          organism = synthetic construct
SEQUENCE: 4
atgggaacgt cacacaccag                                                     20

SEQ ID NO: 5              moltype = DNA  length = 21
FEATURE                   Location/Qualifiers
misc_feature              1..21
                          note = Single strand DNA oligonucleotide
source                    1..21
                          mol_type = other DNA
                          organism = synthetic construct
```

```
SEQUENCE: 5
tacagcgtca ctgtcgatgg c                                             21

SEQ ID NO: 6               moltype = DNA  length = 21
FEATURE                    Location/Qualifiers
misc_feature               1..21
                           note = Single strand DNA oligonucleotide
source                     1..21
                           mol_type = other DNA
                           organism = synthetic construct
SEQUENCE: 6
tcaatcactg tcttgcccca g                                             21

SEQ ID NO: 7               moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 7
aatttggtgt ggacgttggc                                               20

SEQ ID NO: 8               moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 8
ttgtcggtca cttgcactgg                                               20

SEQ ID NO: 9               moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 9
ttgacggtaa ggacggactc                                               20

SEQ ID NO: 10              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 10
acttgcagta ctccccatcg                                               20

SEQ ID NO: 11              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 11
tacttccaca ggtcccacaa                                               20

SEQ ID NO: 12              moltype = DNA  length = 20
FEATURE                    Location/Qualifiers
misc_feature               1..20
                           note = Single strand DNA oligonucleotide
source                     1..20
                           mol_type = other DNA
                           organism = synthetic construct
SEQUENCE: 12
attcctcaca gccaacagtg                                               20

SEQ ID NO: 13              moltype = DNA  length = 20
FEATURE                    Location/Qualifiers
misc_feature               1..20
                           note = Single strand DNA oligonucleotide
source                     1..20
                           mol_type = other DNA
```

```
                        organism = synthetic construct
SEQUENCE: 13
caacagcgac acccactcct                                                       20

SEQ ID NO: 14           moltype = DNA  length = 21
FEATURE                 Location/Qualifiers
misc_feature            1..21
                        note = Single strand DNA oligonucleotide
source                  1..21
                        mol_type = other DNA
                        organism = synthetic construct
SEQUENCE: 14
caccctgttg ctgtagccaa a                                                     21
```

SCAFFOLDS FABRICATED FROM ELECTROSPUN DECELLULARIZED EXTRACELLULAR MATRIX

RELATED APPLICATIONS

This application is a division of U.S. patent application Ser. No. 16/092,787 filed on Oct. 11, 2018, which is a National Phase of PCT Patent Application No. PCT/IL2017/050428 having International Filing Date of Apr. 6, 2017, which claims the benefit of priority of Israel Utility Patent Application No. 245059 filed on Apr. 12, 2016. The contents of the above applications are all incorporated by reference as if fully set forth herein in their entirety.

SEQUENCE LISTING STATEMENT

The XML file, entitled 95246SequenceListing.xml, created on Jan. 23, 2023, comprising 18,751 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates the use of electrospun decellularized extracellular matrix for fabricating scaffolds.

Injured organs or tissues can be replaced via whole organ transplantation. However, major obstacles limit the surgical procedures used for this purpose, including shortage of donors and the need to use immunosuppressive drugs to prevent rejection of the implanted organ. Tissue engineering has emerged as a promising approach to improve or restore the function or shape of a damaged tissue or organ by implantation of polymeric scaffolds, functional cells, or their combination in cell seeded scaffolds. The success of a scaffold for tissue engineering depends on the manufacturing design, the material chosen, and on the accurate understanding of the scaffold's desired characteristics.

A variety of scaffolds were designed and studied in the last two decades for the regeneration of tissues in various organs, using either natural materials or synthetic ones. Moreover, tissue engineering is becoming an important research tool in biology and biomedical research, providing various possibilities for 3D cultures, and thus bridging the gap between 2D cultures and animal models.

Many scaffolds currently developed for tissue engineering are made of synthetic materials, such as PLGA, PMMA and PCL, whose main advantage is that they can be custom-tailored depending on their specific applications. They can be easily designed to match specific properties such as degradability, density and mechanical strength. Their major drawbacks, however, are limited biocompatibility and the absence of any biological activity.

Another approach for tissue engineering is the use of natural polymers such as alginate, collagen and chitosan. These materials are biologically active and typically promote excellent cell adhesion and growth. They are also biodegradable and allow host cells to eventually replace them with their own extracellular matrix. However, scaffolds from biological materials are difficult to control, or finely tune for desired properties. They lack reproducibility and generally have poor mechanical properties, which limits their use.

In recent years, the use of whole decellularized extracellular matrix (ECM) was suggested as the ultimate biomaterial for tissue engineering, as it is the closest mimic to natural cell surroundings, it is bioactive, biodegradable and biocompatible. Whole decellularized ECM has been either used "as-is" or dissolved and refabricated as a gel. However, while this top-down approach provides a more accurate biological environment, it still suffers the drawbacks of natural materials.

In view of these drawbacks, newly developed technologies were employed to produce scaffolds of better controlled properties. One such technology is electrospinning, which provide a bottom-up approach where the fibers are spun into a matte in an organized, homogeneous manner. Nonetheless, electrospinning of biological polymers is not easy since they tend to present the proper degree of viscosity, but lack visco-elasticity, which is required for the electrospinning. Thus, these solutions of natural, biological polymers usually need to be combined with synthetic polymers in order to enhance the visco-elasticity for electrospinning.

U.S. Patent Application No. 20120156250 teaches soluble decellularized ECM.

International Patent Application WO2006/138718 teaches electrospun ECM for generating scaffolds. The ECM is not derived from decellularized tissue.

Additional background art includes Gibson et al., BioMed Research International, 2014, Article ID 469120 and Francis M P et al., 2012. J Biomed Mater Res Part A 2012:100A: 1716-1724.

SUMMARY OF THE INVENTION

According to an aspect of some embodiments of the present invention there is provided a method of generating a scaffold comprising:
(a) homogenizing decellularized extracellular matrix (ECM) in an organic solvent to generate a homogenate of decellularized ECM;
(b) electrospinning the homogenate onto a solid surface thereby generating the scaffold.

According to an aspect of some embodiments of the present invention there is provided a method of generating a scaffold comprising:
(a) dissolving decellularized extracellular matrix (ECM) in an organic solvent to generate a solution of decellularized ECM, wherein the decellularized ECM is derived from an organ selected from the group consisting of heart and pancreas; and
(b) electrospinning the solution onto a solid surface thereby generating the scaffold.

According to an aspect of some embodiments of the present invention there is provided a scaffold generated according to the method described herein.

According to an aspect of some embodiments of the present invention there is provided a scaffold comprising electrospun decellularized ECM of an organ, wherein the decellularized ECM has a similar protein composition to native ECM of the organ.

According to an aspect of some embodiments of the present invention there is provided a scaffold comprising electrospun decellularized ECM, wherein the decellularized ECM is derived from an organ selected from the group consisting of heart and pancreas.

According to an aspect of some embodiments of the present invention there is provided a composition of matter comprising the scaffold described herein and cells seeded on the scaffold.

According to an aspect of some embodiments of the present invention there is provided a method of treating a medical condition which may benefit from cell transplantation in a subject in need thereof, comprising transplanting the scaffold described herein into the subject, thereby treating the medical condition.

According to some embodiments of the invention, the method further comprises decellularizing a tissue of a subject prior to generate the decellularized ECM prior to step (a).

According to some embodiments of the invention, the method further comprises contacting the solution of decellularized ECM with a polymer so as to increase the viscoelasticity of the solution following step (a) and prior to step (b).

According to some embodiments of the invention, the dissolving is effected by homogenization to generate a homogenate of decellularized ECM.

According to some embodiments of the invention, the method further comprises filtering the homogenate of decellularized ECM prior to the electrospinning.

According to some embodiments of the invention, the organic solvent is selected from the group consisting of acetone, N,N-dimethylformamide (DMF), diethylformamide, chloroform, methylethylketone, acetic acid, formic acid, ethanol, 1,1,1,3,3,3-hexa fluoro-2-propanol (HFIP), tetrafluoroethanol, dichloromethane (DCM), tetrahydrofuran (THF), trifluoroacetic acid (TFA), camphorsulfonic acid, dimethyl acetamide, isopropyl alcohol (IPA) and mixtures thereof.

According to some embodiments of the invention, the organic solvent is HFIP.

According to some embodiments of the invention, the polymer is a biocompatible polymer.

According to some embodiments of the invention, the polymer is a hydrophilic polymer.

According to some embodiments of the invention, the polymer is a synthetic polymer.

According to some embodiments of the invention, the synthetic polymer is selected from the group consisting of poly(D,L-lactide) (PLA), poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), polyorthoesters and mixtures thereof.

According to some embodiments of the invention, the synthetic polymer is PEO.

According to some embodiments of the invention, the amount of the PEO in the solution is between 0.05-1% mass.

According to some embodiments of the invention, the decellularized ECM is derived from an organ selected from the group consisting of heart and pancreas.

According to some embodiments of the invention, the decellularized ECM is derived from porcine tissue.

According to some embodiments of the invention, the method further comprises removing the polymer following the electrospinning.

According to some embodiments of the invention, the decellularized ECM has a similar protein composition to native ECM of the organ.

According to some embodiments of the invention, the organ is a heart or a pancreas.

According to some embodiments of the invention, the organ is a human organ or a porcine organ.

According to some embodiments of the invention, the decellularized ECM comprises collagen type I and collagen type III.

According to some embodiments of the invention, the decellularized ECM is devoid of collagen type VI.

According to some embodiments of the invention, the diameter of fibers of the scaffold are between 100-2000 nm.

According to some embodiments of the invention, the diameter of fibers of the scaffold are between 300 to 1500 nm.

According to some embodiments of the invention, the scaffold, when hydrated has fibers of a similar organization to native ECM of the organ.

According to some embodiments of the invention, the scaffold is devoid of a synthetic polymer.

According to some embodiments of the invention, the scaffold has been pre-seeded with cells.

According to some embodiments of the invention, the medical condition is a cardiac disease.

According to some embodiments of the invention, the medical condition is Diabetes.

According to some embodiments of the invention, the scaffold is for use in treating a medical condition which may benefit from cell transplantation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1E are photographs of porcine ECM electrospun in: acidified water and combined with PEO to a mass ratio of (a) 7:1, (b) 8:1, and (c) 14:1. Electrospinning of pcECM dissolved in HFIP (d) without and (e) with 0.1 mass % PEO. Scale bar 100 μm.

FIGS. 11A-11L are SEM images of decellularized pcECM (A,B), and electrospun pcECM scaffolds wetted at different temperatures; scaffold wetted at 37° C. for 1 hr and then at 37° C. overnight (C,D); scaffold wetted at 24° C. for 1 hr and then at 24° C. overnight (E,F); scaffold wetted at 4° C. for 1 hr and then at 4° C. overnight (G,H); scaffold wetted at 24° C. for 1 hr and then at 37° C. overnight (I,J); scaffold wetted at 4° C. for 1 hr and then at 37° C. overnight (K,L).

FIGS. 14A-14D are SEM images of hMSCs seeded on electrospun pcECM scaffold after 4 weeks in culture.

FIGS. 20A-20C are images of cardiomyocytes cultured on pcECM electrospun fibrous scaffolds for 3 weeks, stained with Hoechst 33258 (DNA-blue) and antibodies for Connexin-43 (q), sarcomeric α-actinin-SAA (r), and cardiac troponin I (cTn1, s) cardiac markers (green).

FIGS. 25A-25C are graphs illustrating in vitro immunogenicity studies of pcECM electrospun fibrous scaffolds. Pieces of electrospun pcECM scaffold were used to stimulate RAW macrophages, LPS stimulation was a positive control, and PLGA and non-stimulated cells were negative controls. The level of (A) secreted NO and excreted pro-inflammatory cytokines (B) TNFα and (C) IL1β were evaluated.

FIGS. 26A-26B are graphs illustrating pro-inflammatory cytokine expression of (A) TNFα and (B) IL1β in inguinal lymph nodes of mice that received a subcutaneous implanted electrospun fibrous scaffold from PLGA (dots) and ECM (stripes).

FIGS. 27A-27I are graphs illustrating complete blood counts of mice following subcutaneous implantation of electrospun PLGA and electrospun pcECM scaffolds. Number of white blood cells (WBC, A), and red blood cells (RBC, B), hematocrit volume (C), hemoglobin concentration (D), mean corpuscular volume (MCV, E) mean corpuscular hemoglobin (MCH, F), mean corpuscular hemoglobin concentration (MCHC, G) number of neutrophils (H), and lymphocytes (I), all plotted over a period of four weeks following implantation. Dashed lines represent ranges of normal blood values for C57 black mice (Charles River Laboratories).

DESCRIPTION OF SPECIFIC EMBODIMENTS OF THE INVENTION

Figure 2A:
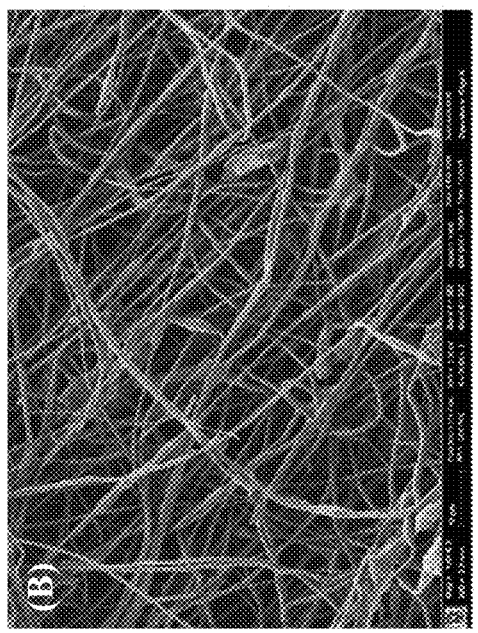
FIGS. 2A-2D are HR-SEM images of porcine cardiac ECM (pcECM) fibers at (A) 200 X, (B) 1 kX, (C) 5 kX, and (D) 10 kX.

The present invention, in some embodiments thereof, relates to the use of electrospun decellularized extracellular matrix for fabricating scaffolds.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Scaffolds developed for tissue repair and regenerative therapy require appropriate structure and functional characteristics native to the tissue or organ under consideration. Native ECM is a promising candidate for this purpose, as each tissue is comprised of a unique combination and 3D structure of macromolecules that provides cells with the necessary cues and mechanical support.

In recent years, the use of whole decellularized extracellular matrix (ECM) was suggested as the ultimate biomaterial for tissue engineering, as it is the closest mimic to natural cell surroundings, it is bioactive, biodegradable and biocompatible.

However, scaffolds from decellularized ECM are difficult to control, or finely tune for desired properties. They lack reproducibility and generally have poor mechanical properties, which limits their use.

In order to overcome these limitations, the present inventors now propose electrospinning decellularized ECM for fabrication of biological scaffolds. This would not only provide cells with the natural environment attributed to the ECM, but also provide control over the structure of the fibrous ECM network, allowing the design of scaffolds with specific properties such as degradability, density and mechanical strength.

Whilst reducing the present invention to practice, the present inventors generated scaffolds which were fabricated from ECM isolated from a single organ—pancreas or heart.

As is illustrated herein under and in the examples section which follows, the present inventors show that the cells seeded on the scaffolds had a polypeptide composition similar to the native ECM of the organ from which it was derived—Tables 1-2. The average fiber diameter of the scaffold ranged from 300 to 1500 nm. Furthermore, upon hydration fiber organization and diameter became similar to that of native ECM of the organ from which it was derived (FIGS. 11A-11B). The inventors further demonstrate that cells seeded on the scaffolds were capable of surviving for at least four weeks (FIGS. 13, 17, 19 and 23). Scaffolds fabricated according to the disclosed methods were shown to be non-immunogenic (FIGS. 25-27).

Thus, according to one aspect of the present invention, there is provided a method of generating a scaffold comprising:

(a) dissolving decellularized extracellular matrix (ECM) of an organ in an organic solvent to generate a solution of decellularized ECM; and
(b) electrospinning the solution onto a solid surface thereby generating the scaffold.

As used herein the phrase "decellularized ECM" refers to the extracellular matrix which supports tissue organization (e.g., a natural tissue) and underwent a decellularization process (i.e., a removal of all cells from the organ) and is thus completely devoid of any cellular components.

The decellularized ECM typically comprises a plurality of polypeptides (e.g. collagens). For example, the decellularized ECM comprises collagen alpha-2(I), collagen alpha-1 (III) and collagen alpha-1(I). Additionally, the decellularized ECM may also comprise collagen alpha-2(IV), collagen alpha-1(V) and collagen alpha-1(II) (or fragments thereof) Preferably, the amount of collagen alpha-2(I), collagen alpha-1(III) and collagen alpha-1(I) is greater in the decellularized ECM of this aspect of the present invention than collagen alpha-2(IV), collagen alpha-1(V) and collagen alpha-1(II).

Additionally, the decellularized ECM may also comprise smaller amounts of collagen alpha-2(VI), collagen alpha-3 (VI) and collagen alpha-1(VI) or collagen alpha-1(IV) (or fragments thereof). Preferably, the amount of collagen alpha-2(I), collagen alpha-1(III) and collagen alpha-1(I) is greater in the decellularized ECM of this aspect of the present invention than collagen alpha-2(VI), collagen alpha-3(VI) and collagen alpha-1(VI) or collagen alpha-1(IV).

The phrase "completely devoid of any cellular components" as used herein refers to being more than 90%, 91%, 92%, 93%, 94%, 95%, 96%, 97%, 98%, 99%, (e.g., 100%) devoid of the cellular components present in the natural (e.g., native) tissue. As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue. It will be appreciated that due to the removal of all cellular components from the tissue, such a decellularized matrix cannot induce an immunological response when implanted in a subject.

The phrase "extracellular matrix (ECM)" as used herein, refers to a complex network of materials produced and secreted by the cells of the tissue into the surrounding extracellular space and/or medium and which typically together with the cells of the tissue impart the tissue its mechanical and structural properties. Generally, the ECM includes fibrous elements (particularly collagen, elastin, or reticulin), cell adhesion polypeptides (e.g., fibronectin, laminin and adhesive glycoproteins), and space-filling molecules [usually glycosaminoglycans (GAG), proteoglycans].

According to embodiments of the present invention the decellularized ECM is derived from cardiac or pancreatic tissue.

Other tissues contemplated by the present inventors include brain tissue, bone tissue, muscle, liver, kidney, blood vessel, lung and placenta.

In other embodiments, the decellularized ECM is not derived from fat tissue.

In still other embodiments, the decellularized ECM is not MATRIGEL or derived from isolated basement membranes.

The ECM may be derived from an autologous or non-autologous subject (e.g., from allogeneic or even xenogeneic tissue, due to non-immunogenicity of the resultant decellularized matrix). The tissue is removed from the subject [e.g., an animal, preferably a mammal, such as a pig, rat, monkey or chimpanzee, or alternatively, a deceased human being (shortly after death)] and washed e.g. in a sterile saline solution (0.9% NaCl, pH=7.4) or phosphate buffered saline (PBS), which can be supplemented with antibiotics such as Penicillin/Streptomycin 250 units/ml. Although whole tissues can be used, for several applications, segments of tissues may be cut e.g. sliced. Such tissue segments can be of various dimensions, depending on the original tissue used and the desired application.

To remove the vasculature surrounding and feeding the tissue, the tissue may be washed at room temperature by agitation in large amounts (e.g., 50 ml per each gram of tissue segment) of EDTA solution (0.5-10 mM, pH-7.4).

Next, the tissue is subjected to a hypertonic or hypotonic buffer to thereby obtain increased intercellular space within the tissue.

The hypertonic buffer used by the present invention can be any buffer or solution with a concentration of solutes that is higher than that present in the cytoplasm and/or the intercellular liquid within the tissue [e.g., a concentration of NaCl which is higher than 0.9% (w/v)]. Due to osmosis, incubation of the tissue with the hypertonic buffer results in increased intercellular space within the tissue.

According to another embodiment, peracetic acid is used to decellularize the tissue.

Preferably, the hypertonic buffer used by the method according to this aspect of the present invention includes sodium chloride (NaCl) at a concentration which is higher than 0.9% (w/v), preferably, higher than 1% (w/v), preferably, in the range of 1-1.2% (w/v), e.g., 1.1% (w/v).

Preferably, the hypotonic buffer used by the method according to this aspect of the present invention includes sodium chloride (NaCl) at a concentration which is lower than 0.9% (w/v), lower than 0.8% (w/v), lower than 0.7% (w/v), preferably, in the range of 0.6-0.9% (w/v), e.g., 0.7% (w/v).

According to this aspect of the present invention, the tissue is subjected to the hypertonic or hypotonic buffer for a time period leading to the biological effect, i.e., cell shrinkage which leads to increased intercellular space within the tissue.

According to a particular embodiment, the tissue is contacted with a hypertonic buffer (e.g. 1.1% w/v) and subsequently contacted with a hypotonic buffer (e.g. 0.7% w/v). This procedure may be repeated for two or more cycles.

Preferably, the hypotonic buffer used by the method according to this aspect of the present invention includes sodium chloride (NaCl) at a concentration which is lower than 0.9% (w/v), lower than 0.8% (w/v), lower than 0.7% (w/v), preferably, in the range of 0.6-0.9% (w/v), e.g., 0.7% (w/v).

Following incubation with the hypertonic/hypotonic buffer, the tissue is further subjected to an enzymatic proteolytic digestion which digests all cellular components within the tissue yet preserves the ECM components (e.g., collagen and elastin) and thus results in a matrix which exhibits the mechanical and structural properties of the original tissue ECM. It will be appreciated that measures are taken to preserve the ECM components while digesting the cellular components of the tissue. These measures are further described hereinbelow and include, for example, adjusting the concentration of the active ingredient (e.g., trypsin) within the digestion solution as well as the incubation time.

Proteolytic digestion according to this aspect of the present invention can be effected using a variety of proteolytic enzymes. Non-limiting examples of suitable proteolytic enzymes include trypsin and pancreatin which are available from various sources such as from Sigma (St Louis, MO, USA). According to one preferred embodiment of this aspect of the present invention, proteolytic digestion is effected using trypsin.

Digestion with trypsin is preferably effected at a trypsin concentration ranging from 0.01-0.25% (w/v), more preferably, 0.02-0.2% (w/v), more preferably, 0.05-0.1 (w/v), even more preferably, a trypsin concentration of about 0.05% (w/v). For example, a trypsin solution containing 0.05% trypsin (w/v; Sigma), 0.02% EDTA (w/v) and antibiotics (Penicillin/Streptomycin 250 units/ml), pH=7.2] may be used to efficiently digest all cellular components of the tissue.

It will be appreciated that for efficient digestion of all cellular components of the tissue, each of the tissue segments may be placed in a separate vessel containing the digestion solution (e.g., a trypsin solution as described hereinabove) in a ratio of 40 ml digestion solution per each gram of tissue. Preferably, while in the digestion solution, the tissue segments are slowly agitated (e.g., at about 150 rpm) to enable complete penetration of the digestion solution to all cells of the tissue.

It should be noted that the concentration of the digestion solution and the incubation time therein depend on the type of tissue being treated and the size of tissue segments utilized and those of skilled in the art are capable of adjusting the conditions according to the desired size and type of tissue.

Preferably, the tissue segments are incubated for at least about 20 hours, more preferably, at least about 24 hours. Preferably, the digestion solution is replaced at least once such that the overall incubation time in the digestion solution is at least 40-48 hours.

Next, the cellular components are removed from the tissue. Removal of the digested components from the tissue can be effected using various wash solutions, such as detergent solutions (e.g., ionic and non ionic detergents such as SDS Triton X-100, Tween-20, Tween-80) which can be obtained from e.g., Sigma (St Louis, MO, USA) or Biolab (Atarot, Israel, Merck Germany).

Preferably, the detergent solution used by the method according to this aspect of the present invention includes TRITON-X-100 (available from Merck). For efficient removal of all digested cellular components, TRITON-X-100 is provided at a concentration range of 0.05-2.5% (v/v), more preferably, at 0.05-2% (v/v), more preferably at 0.1-2% (v/v), even more preferably at a concentration of 1% (v/v).

Preferably, for optimized results, the detergent solution includes also ammonium hydroxide, which together with the TRITON-X-100, assists in breaking and dissolving cell nuclei, skeletal proteins, and membranes.

Preferably, ammonium hydroxide is provided at a concentration of 0.05-1.5% (v/v), more preferably, at a concentration of 0.05-1% (v/v), even more preferably, at a concentration of 0.1-1% (v/v) (e.g., 0.1%).

The concentrations of TRITON-X-100 and ammonium hydroxide in the detergent solution may vary, depending on the type and size of tissue being treated and those of skills in the art are capable of adjusting such concentration according to the tissue used.

Incubation of the tissue (or tissue segments) with the detergent solution can last from a few minutes to hours to even several days, depending on the type and size of tissue and the concentration of the detergent solution used and those of skills in the art are capable of adjusting such incubation periods. Preferably, incubation with the detergent solution is effected for at least 24-72 hours. According to one embodiment, 2-4 cycles of incubation with the detergent solution are performed until no foam is observed, such that the total incubation time may be between about 150-200 hours.

Although as described hereinabove, incubation with the detergent solution enables the removal of cell nuclei, proteins and membrane, the method according to this aspect of the present invention optionally includes an additional step of removing nucleic acids (as well as residual nucleic acids) from the tissue to thereby obtain a nucleic acid—free tissue. As used herein the phrase "nucleic acid—free tissue" refers to a tissue being more than 99% free of any nucleic acid or fragments thereof as determined using conventional methods (e.g., spectrophotometry, electrophoresis). Such a step utilizes a DNase solution (and optionally also an RNase solution). Suitable nucleases include DNase and/or RNase [Sigma, Bet Haemek Israel, 20 µg/ml in Hank balance salt solution (HBSS)].

The above described detergent solution is preferably removed by subjecting the ECM to several washes in water or saline (e.g., at least 10 washes of 30 minutes each, and 2-3 washes of 24 hours each), until there is no evident of detergent solution in the matrix.

Optionally, the decellularized ECM is then sterilized. Sterilization of the decellularized ECM may be effected using methods known in the art (e.g. 70% ethanol).

Typically, in order to carry out solubilization of the decellularized ECM, it is frozen (e.g. in liquid nitrogen), cut into small pieces (e.g. crumbled, crushed or ground) and then lyophilized.

The lyophilized decellularized ECM is then solubilized in an organic solvent.

Exemplary organic solvents contemplated by the present inventors include, but are not limited to acetone, N,N-dimethylformamide (DMF), diethylformamide, chloroform, methylethylketone, acetic acid, formic acid, ethanol, 1,1,1,3,3,3-hexa fluoro-2-propanol (HFIP), tetrafluoroethanol, dichloromethane (DCM), tetrahydrofuran (THF), trifluoroacetic acid (TFA), camphorsulfonic acid, dimethyl acetamide, isopropyl alcohol (IPA) and mixtures thereof.

Exemplary concentrations of decellularized ECM in the organic solvent contemplated by the present invention are between 0.005 g/mL to 0.5 g/mL—for example about 0.05 g/mL.

According to a particular embodiment, the organic solvent is HFIP.

In order to aid in the solubilization process, following or concomitant with the solubilization, the decellularized ECM may be homogenized.

Typically, the homogenization is effected in the presence of a rigid grinding media which is preferably spherical or particulate in form having an average size less than about 10 mm (e.g. between 2-10 mm) and, more preferably between 2-7 mm. The selection of material for the grinding media is not believed to be critical. Zirconium oxide, such as 95% ZrO stabilized with magnesia, zirconium silicate, ceramic, stainless steel, titania, alumina, 95% ZrO stabilized with yttrium, glass grinding media, and polymeric grinding media are exemplary grinding materials.

The grinding media can comprise particles that are preferably substantially spherical in shape, e.g., beads, consisting essentially of polymeric resin or other suitable material. Alternatively, the grinding media can comprise a core having a coating of a polymeric resin adhered thereon.

The homogenization may be performed using a homogenizer e.g. a bead homogenizer such as g a Precellys™24 bead. The homogenization should be effected for a length of time until the solution appears homogeneous (at 6000 rpm for 5 second intervals, for at least 6 intervals).

Optionally, to improve homogenization the homogenate may be sonicated. In one embodiment decellularized ECM derived from the pancreas is sonicated (for example, for no more than three minutes) following the homogenization step.

Following homogenization, the homogenate may be mixed for a suitable length of time (e.g. 1 day, two days, three days or more) by placing on a rotator.

To remove any particulate matter, the homogenate may be filtered (e.g. using glass wool).

As mentioned, following the dissolution of the decellularized ECM, the solution is then electrospun.

The present invention contemplates contacting the solution of decellularized ECM with a polymer so as to increase the viscoelasticity of the solution prior to the electro spinning process.

In one embodiment, the polymer is a biocompatible polymer.

In another embodiment, the polymer is a hydrophilic polymer.

Preferably, the polymer is a synthetic polymer.

Exemplary synthetic polymers contemplated by the present invention include, but are not limited to poly(D,L-lactide) (PLA), poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), polyorthoesters and mixtures thereof.

According to a particular embodiment, the polymer is PEO.

The amount of polymer (e.g. PEO) in the solution is typically between 0.05-1% mass, and more preferably between 0.05-0.5% mass—for example about 0.1%.

As used herein, the term "electrospinning" refers to a technology which produces electrospun fibers (e.g. nanofibers and/or microfibers) from a polymer solution. During this process, the dissolved polymers are placed in a dispenser. An electrostatic field is employed to generate a positively charged jet from the dispenser to the collector. Thus, a dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Reverse polarity for establishing motions of a negatively charged jet from the dispenser to the collector is also contemplated. At the critical voltage, the charge repulsion begins to overcome the surface tension of the liquid drop. The charged jets depart from the dispenser and travel within the electrostatic field towards the collector. Moving with high velocity in the inter-electrode space, the jet stretches and the solvent therein evaporates, thus forming fibers which are collected on the collector forming the electrospun scaffold.

Several parameters may affect the diameter of the fiber, these include, the size of the dispensing hole of the dispenser, the dispensing rate, the strength of the electrostatic field, the distance between the dispenser and/or the concentration of the polymer used for fabricating the electro spun fiber.

In one embodiment, the fibers are electrospun with a voltage of 1-20 kV, for example between 5-10 kV and more preferably between 8-9 kV. The hole of the dispenser may be between 20-30 gauge (e.g. a 23 gauge blunt needle), and the distance from needle to collector may be between 1-20 cm, more preferably between 6-10 cm, with a flow rate between 0.1-3 ml/hr, more preferably between 0.5-1 ml/hr.

The electrospun fibers are collected on a solid surface such as a metal surface or a polymeric surface. In one embodiment, the fibers are collected on a metal surface coated with a polymer (for example polyethylene).

As mentioned, in some embodiments a polymer is added to the dissolved decellularized ECM. The present invention contemplates removing the polymer following the electrospinning, especially if the polymer is not biocompatible. When the polymer is a hydrophilic polymer, it may be removed simply by rinsing in an aqueous solution.

In one aspect of the present invention, the scaffolds comprise electrospun decellularized ECM of an organ, wherein the decellularized ECM has a similar protein composition to native ECM of the organ.

As used herein, the term "scaffold" refers to a three dimensional structure comprising a biocompatible material that provides a surface suitable for adherence and proliferation of cells. A scaffold may further provide mechanical stability and support.

The dimensions and shape of the scaffold will vary according to the disease or injury being treated. It will be further appreciated that the dimensions of the scaffold will vary according to the size of the subject.

Typically, the scaffolds of the present invention are porous. The porosity of the scaffold may be controlled by altering the parameters used for electrospinning as known to those skilled in the art. The minimum pore size and degree of porosity is dictated by the need to provide enough room for the cells and for nutrients to filter through the scaffold to the cells. The maximum pore size and porosity is limited by the ability of the scaffold to maintain its mechanical stability after seeding.

According to a preferred embodiment of this aspect of the present invention, the scaffold has an average pore diameter of about 10-40 μm.

According to this aspect the decellularized ECM may be derived from any tissue such as cardiac tissue, pancreatic tissue, blood vessel tissue, muscle tissue, liver tissue, kidney tissue, brain tissue, bone tissue, lung and placenta.

Preferably, the decellularized ECM is derived from pancreatic tissue or cardiac tissue.

When the decellularized ECM is derived from cardiac tissue, decellularized ECM maintains the protein composition of native cardiac ECM, or at least has a similar protein composition to native cardiac ECM. Thus, for example the majority of the collagen of the decellularized ECM is collagen type I and type III, since that is the most abundant collagen in cardiac tissue.

In another embodiment, the decellularized ECM is devoid of collagen type VI.

When the decellularized ECM is derived from pancreatic tissue, decellularized ECM maintains the protein composition of native pancreatic ECM or at least has a similar protein composition to native pancreatic ECM. Thus, for example the majority of the collagen of the decellularized ECM are collagens type I and type III, since that is the most abundant collagen in pancreatic tissue.

In another aspect, the scaffold comprises electrospun decellularized ECM, wherein the decellularized ECM is derived from an organ selected from the group consisting of heart and pancreas.

The scaffold comprises fibers of different thickness. When imaged using imageJ analyses, thick fibers may have an average diameter between 100-2000 nm, more preferably between 300-1500 nm (which corresponds to type I collagen fibers in native ECM) and thin fibers have an average diameter of between 30-80 nm (which corresponds to type III collagen fibers in native ECM).

Thus, the present inventors contemplate that scaffolds generated according to methods described herein are of a similar protein composition to native ECM, have a similar fiber diameter to native ECM and/or have a similar organization to native ECM when hydrated.

According to particular embodiments, the scaffolds are devoid of a synthetic polymer (do not comprise more than trace amounts of synthetic polymer).

Therapeutic compounds or agents that modify cellular activity can also be incorporated (e.g. attached to, coated on, embedded or impregnated) into the scaffold material. Furthermore, the present inventors contemplate embedding particles which release the therapeutic compounds or agents into the scaffold. Campbell et al (US Patent Application No. 20030125410) which is incorporated by reference as if fully set forth by reference herein, discloses methods for fabrication of 3D scaffolds for stem cell growth, the scaffolds having preformed gradients of therapeutic compounds. The scaffold materials, according to Campbell et al, fall within the category of "bio-inks". Such "bio-inks" are suitable for use with the compositions and methods of the present invention.

Exemplary agents that may be incorporated into the scaffold of the present invention include, but are not limited to those that promote cell adhesion (e.g. fibronectin, integrins), cell colonization, cell proliferation, cell differentiation, anti-inflammatories, cell extravasation and/or cell migration. Thus, for example, the agent may be an amino acid, a small molecule chemical, a peptide, a polypeptide, a protein, a DNA, an RNA, a lipid and/or a proteoglycan.

Proteins that may be incorporated into the scaffolds of the present invention include, but are not limited to extracellular matrix proteins, cell adhesion proteins, growth factors, cytokines, hormones, proteases and protease substrates. Thus, exemplary proteins include vascular endothelial-derived growth factor (VEGF), activin-A, retinoic acid, epidermal growth factor, bone morphogenetic protein, TGFβ, hepatocyte growth factor, platelet-derived growth factor, TGFα, IGF-I and II, hematopoetic growth factors, heparin binding growth factor, peptide growth factors, erythropoietin, interleukins, tumor necrosis factors, interferons, colony stimulating factors, basic and acidic fibroblast growth factors, nerve growth factor (NGF) or muscle morphogenic factor (MMP). The particular growth factor employed should be appropriate to the desired cell activity. The regulatory effects of a large family of growth factors are well known to those skilled in the art.

The scaffolds of the invention may be seeded with cells, including for example primary cells, cultured cells, single cell suspensions of cells, clusters of cells e.g. islets, cells which are comprised in tissues and/or organs etc.

Cells can be seeded in the scaffold by static loading, or, more preferably, by seeding in stirred flask bioreactors (scaffold is typically suspended from a solid support), in a rotating wall vessel, or using direct perfusion of the cells in medium in a bioreactor. Highest cell density throughout the scaffold is achieved by the latter (direct perfusion) technique.

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components. An exemplary gel is Matrigel™, from Becton-Dickinson. Matrigel™ is a solubilized basement membrane matrix extracted from the EHS mouse tumor (Kleinman, H. K., et al., Biochem. 25:312, 1986). The primary components of the matrix are laminin, collagen I, entactin, and heparan sulfate proteoglycan (perlecan) (Vukicevic, S., et al., Exp. Cell Res. 202:1, 1992). Matrigel™ also contains growth factors, matrix metalloproteinases (MMPs [collagenases]), and other proteinases (plasminogen activators [PAs]) (Mackay, A. R., et al., BioTechniques 15:1048, 1993). The matrix also includes several undefined compounds (Kleinman, H. K., et al., Biochem. 25:312, 1986; McGuire, P. G. and Seeds, N. W., J. Cell. Biochem. 40:215, 1989), but it does not contain any detectable levels of tissue inhibitors of metalloproteinases (TIMPs) (Mackay, A. R., et al., BioTechniques 15:1048, 1993).

Alternatively, the gel may be growth-factor reduced Matrigel, produced by removing most of the growth factors from the gel (see Taub, et al., Proc. Natl. Acad. Sci. USA (1990); 87 (10:4002-6). In another embodiment, the gel may be a collagen I gel, alginate or agar. Such a gel may also include other extracellular matrix components, such as glycosaminoglycans, fibrin, fibronectin, proteoglycans, and glycoproteins. The gel may also include basement membrane components such as collagen IV and laminin. Another gel contemplated by the present inventors is an ECM gel—see for example Uriel et al., Tissue Engineering: Part C, Volume 15, Number 3, 2009, Mary Ann Liebert, Inc., DOI: 10.1089=ten.tec.2008.0309.

Enzymes such as proteinases and collagenases may be added to the gel, as may cell response modifiers such as growth factors and chemotactic agents.

The cells may be derived from any organism including for example mammalian cells, (e.g. human), plant cells, insect cells, algae cells, fungal cells (e.g. yeast cells), prokaryotic cells (e.g. bacterial cells).

According to a particular embodiment the cells comprise stem cells—e.g. adult stem cells such as mesenchymal stem cells or pluripotent stem cells such as embryonic stem cells or induced pluripotent stem cells. The stem cells may be modified so as to undergo ex vivo differentiation.

According to a particular embodiment, the cells are preferably intact (i.e. whole), and preferably viable, although it will be appreciated that pre-treatment of cells, such as generation of cell extracts or non-intact cells are also contemplated by the present invention.

The cells may be fresh, frozen or preserved in any other way known in the art (e.g. cryopreserved).

According to another embodiment, the cells are derived from the pancreas or the heart.

The tissue from which the decellularized extracellular matrix is produced may be selected (i.e. matched) according to the cells which are incorporated therein.

Thus, for example when the cells are derived from the pancreas—e.g. pancreatic beta cells (or modified so as to imitate pancreatic beta cells), according to certain embodiments, the tissue from which the decellularized extracellular matrix is produced is pancreatic tissue.

In a similar fashion, when the cells are derived from cardiac tissue—e.g. cardiac myocardial cells (or modified so as to imitate cardiac myocardial cells), according to certain embodiments, the tissue from which the decellularized extracellular matrix is produced is cardiac myocardial tissue.

Typically, the cells secrete a factor (e.g. a polypeptide) that is useful for the treatment of a disease.

Such factors include for example, hormones including but not limited to insulin, thyroxine, growth hormone, testosterone, oestrogen, erythropoietin and aldosterone; enzymes, including but not limited to lysosomal enzyme such as glucocerebrosidase (GCD), acid sphingomyelinase, hexosaminidase, α-N-acetylgalactosaminidise, acid lipase, α-galactosidase, α-L-iduronidase, iduronate sulfatase, α-mannosidase, sialidase, α fucosidase, $G_{M1}$-β-galctosidase, ceramide lactosidase, arylsulfatase A, β galactosidase and ceramidase; clotting factors such as factor VIII.

According to a preferred embodiment, the cells secrete insulin.

As used herein, the term "insulin" refers to an insulin obtained by synthesis or recombination, in which the peptide sequence is the sequence of human insulin, includes the allelic variations and the homologs. The polypeptide sequence of the insulin may be modified to improve the function of the insulin (e.g. long lasting).

According to one embodiment, the cells are naïve (non-genetically modified).

The present invention also contemplates use of cells which have been genetically modified to express a recombinant protein. The recombinant protein may be a therapeutic protein or may promote in vivo longevity (AM, adrenomedullin, Jun-Ichiro et al. Tissue Eng. 2006) or may promote neurotransmitter release (e.g., such as by transfecting with tyrosine hydroxylase).

Examples of therapeutic, recombinant proteins that may be expressed in the cells of the present invention include, but are not limited to an antibody, insulin, human growth hormone (rHGH), follicle stimulating hormone, factor VIII, erythropoietin, Granulocyte colony-stimulating factor (G-CSF), alpha-glactosidase A, alpha-L-iduronidase (rhIDU; laronidase), N-acetylgalactosamine-4-sulfatase (rhASB; galsulfase) Tissue plasminogen activator (TPA), Glucocerebrosidase, Interferon (IF) Interferon-beta-1a, Interferon beta-1b, Insulin-like growth factor 1 (IGF-1), somatotropin (ST) and chymosin.

Other examples of exogenous polynucleotides which may be expressed in accordance with the present teachings include, but are not limited to, polypeptides such as peptide hormones, antibodies or antibody fragments (e.g., Fab), enzymes and structural proteins or dsRNA, antisense/ribozyme transcripts which can be directed at specific target sequences (e.g., transcripts of tumor associated genes) to thereby downregulate activity thereof and exert a therapeutic effect. Similarly, protective protein antigens for vaccination (see, for example, Babiuk S et al J Control Release 2000; 66:199-214) and enzymes such as fibrinolysin for treatment of ischemic damage (U.S. Pat. No. 5,078,995 to Hunter et al) may expressed in the cells for transdermal or transcutaneous delivery. The therapeutic protein can also be a prodrug.

Thus, according to another aspect of the present invention there is provided a method of treating a medical condition (e.g., pathology, disease, syndrome, trauma) which may benefit from cell transplantation in a subject in need thereof comprising transplanting the scaffold of the present invention into the subject.

As used herein the term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. Preferably, the term "treating" refers to alleviating or diminishing a symptom associated with a disease or trauma which may benefit from cell transplantation. Preferably, treating cures, e.g., substantially eliminates, the symptoms associated with the medical condition.

As used herein "a medical condition which may benefit from cell transplantation" refers to any medical condition which may be alleviated by administration of the scaffold (cell-seeded, or non cell-seeded) of the present invention.

Examples of such medical conditions include, but are not limited to, stem cell deficiency, heart disease, neurodegenerative diseases, glaucoma neuropathy, Parkinson's disease, cancer, Schizophrenia, Alzheimer's disease, stroke, burns, loss of tissue, loss of blood, anemia, autoimmune disorders, diabetes, arthritis, graft vs. host disease (GvHD), neurodegenerative disorders, chronic pain, autoimmune encephalomyelitis (EAE), systemic lupus erythematosus (SLE), rheumatoid arthritis, systemic sclerosis, Sjorgen's syndrome, multiple sclerosis (MS), Myasthenia Gravis (MG), Guillain-Barré Syndrome (GBS), Hashimoto's Thyroiditis (HT), Graves's Disease, Insulin Dependent Diabetes Melitus (IDDM) and Inflammatory Bowel Disease.

As mentioned, the method may be applied to repair cardiac tissue in a human subject having a cardiac disorder so as to thereby treat the disorder. The method can also be applied to repair cardiac tissue susceptible to be associated with future onset or development of a cardiac disorder so as to thereby inhibit such onset or development.

The present invention can be advantageously used to treat disorders associated with, for example, necrotic, apoptotic, damaged, dysfunctional or morphologically abnormal myocardium. Such disorders include, but are not limited to, ischemic heart disease, cardiac infarction, rheumatic heart disease, endocarditis, autoimmune cardiac disease, valvular heart disease, congenital heart disorders, cardiac rhythm disorders, impaired myocardial conductivity and cardiac insufficiency.

According to one embodiment, the method according to this aspect of the present invention can be advantageously used to efficiently reverse, inhibit or prevent cardiac damage caused by ischemia resulting from myocardial infarction.

According to another embodiment, the method according to this aspect of the present invention can be used to treat cardiac disorders characterized by abnormal cardiac rhythm, such as, for example, cardiac arrhythmia.

As used herein the phrase "cardiac arrhythmia" refers to any variation from the normal rhythm of the heart beat, including, but not limited to, sinus arrhythmia, premature heat, heart block, atrial fibrillation, atrial flutter, pulsus alternans and paroxysmal tachycardia.

According to another embodiment, the method according to this aspect of the present invention can be used to treat impaired cardiac function resulting from tissue loss or dysfunction that occur at critical sites in the electrical conduction system of the heart, that may lead to inefficient rhythm initiation or impulse conduction resulting in abnormalities in heart rate.

The term or phrase "transplantation", "cell replacement", "implantation" or "grafting" are used interchangeably herein and refer to the introduction of the cells of the present invention to target tissue.

As used herein the term "subject" refers to any subject (e.g., mammal), preferably a human subject.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture"

Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other procedures used in the context of the present invention are of the mechanical engineering and electrospinning realm. Other general references are provided throughout this document. The procedures therein are believed to be well known in the art and are provided for the convenience of the reader. All the information contained therein is incorporated herein by reference.

Example 1

Materials and Methods

Decellularization procedure: Porcine cardiac or pancreas ECM was decellularized and sterilized according to a previously published protocol.[21] (Chaimov 2016, PMID: 27476611) Briefly, tissue of healthy commercial slaughter-weight pigs was isolated for the decellularization procedure. The procedure was comprised of two cycles with the following stages: Alternating hyper/hypo tonic NaCl solutions; enzymatic treatment using trypsin; and detergent washes with Triton-X-100.

ECM dissolution: Decellularized, sterilized ECM was frozen in liquid nitrogen and crushed in a cryogenic tissue grinder (BioSpec, Bartlesville, Okla., USA), and subsequently placed on a lyophilizer until dry. Lyophillized ECM was dissolved in hexafluoroisopropanol (HFIP) to a concentration of 0.05 g/ml and homogenized using ZrO beads on a Precellys™ 24 bead homogenizer (Bertin Technologies, Rockville, MD, USA) at 6000 rpm until the solution appeared homogeneous, Pancreatic ECM was sonicated for up to 3 minutes following the homogenization. Solutions were then filtered through glass fibers prior to electrospinning.

Electrospinning Conditions

PEO was added only to solutions of porcine cardiac (pcECM) to obtain a final solution of 0.1 mass % PEO. The porcine pancreatic ECM (ppECM) or pcECM/PEO solution was electrospun using a custom built electrospinning device. The fibers were electrospun with a voltage of 8-9 kV, and collected on a thin film of polyethylene covering a rotating aluminum disc with a diameter of 9 cm and a width of 11 mm. The capillary was a 23 gauge blunt needle, and the distance from needle to collector was 6-10 cm, and the flow rate was 0.5-1 ml/hr. Fibers were collected until a thick matte was observed. The matte was then peeled off the surface and placed in a dry environment. PEO was removed from pcECM matrices by washing in a water-based solution, while the pcECM fibers remained intact.

SEM: Samples were visualized using a FEG Zeiss Ultra Plus high resolution scanning electron microscope (HR-SEM, Zeiss, Jena, Germany), equipped with a Schotkky field emission electron gun to provide high level brightness that overcomes charging of uncoated non-conductive specimens. The microscope is also equipped with a charge compensation system to further enhance this effect. Samples were mounted on aluminum stabs stubs using adhesive carbon double-sided tape, and images were captured at 1.3 kV accelerating voltage using a combination of the in-lens type and SE2 type detectors. The analysis of fiber diameters was determined by taking an average of 20 measurements chosen at random across images take from 6 randomly selected areas of the scaffold that were at least a magnification of 5 kX. Digital images were analyzed evaluated using ImageJ software (version 1.49) and Porometric software (PhenomWorld).

Wetted scaffolds were visualized using a Phenom ProX desktop SEM (PhenomWorld, Eindhoven, Netherlands), equipped with a temperature controlled sample holder (Deben UK Ltd., Suffolk, UK). Samples were mounted on aluminum stabs using tissue freezing medium (Ted Pella, Inc., CA, USA), and cooled to −24° C. Images were captured at 15 kV accelerating voltage.

Contact angle: The contact angle of the ECM electrospun fibrous scaffolds was determined by disposing a droplet of near 1 mm in diameter onto the surface. A static image was then captured with an Artcam 130 MIBW camera (Artray Co. Ltd., Tokyo, Japan). The contact angle was then calculated using a special procedure developed in MatLab R2014a software (Mathworks, Natick, MA, USA).

FTIR: Fourier transform infrared spectroscopy (FTIR) spectra of the electrospun ECM scaffolds and decellularized ECM were recorded using a Thermo 6700 FTIR instrument, equipped with a Smart iTR Attenuated Total Reflectance (ATR) diamond plate, in the wave-number range of 500-3500 cm-1 (64 scans at a resolution of 4 cm-1, n=4). Data were evaluated using OMNIC™ series software (version 8, Thermoscientific). Secondary structure of proteins was determined by Fourier deconvolution of their amid I band.

TGA: Thermal gravimetric analysis (TGA) data were obtained using a TGA-Q5000 system (TA instruments, USA). Samples were heated from RT at a rate of 20° C. $\text{min}^{-1}$ under nitrogen atmosphere to a final temperature of 600° C. Data were analyzed using TA Universal Analysis Software (TA Instruments, New Castle, DE, USA).

Electrospun ECM scaffold composition: An analysis of the protein composition was performed at the Proteomics Center, Technion—Israel Institute of Technology. Samples were digested by trypsin and the resulting peptides were analyzed by LC-MS/MS. After which, the peptide mix was fractionated by HPLC and electro-sprayed onto an ion-trap mass spectrometer, in order to determine the proteins' mass. The peptides were further fragmented by collision induced dissociation and analyzed again, for additional analysis and identification. Peptides were analyzed and identified using Proteome Discoverer™ software (Thermo-Scientific) against the porcine part of the UniProt database.

Mechanical testing: Tensile properties of the electrospun 3D fibrous scaffolds were determined using a dynamic mechanical analyzer (DMA) Q800 (TA Instruments, New Castle, DE, USA) at ambient conditions. Scaffolds were cut into 4.3±0.2 mm by 6.7±0.3 mm rectangular specimens, mounted vertically between two mechanical gripping units, in a physiological buffer. An extension rate of 2% $\text{min}^{-1}$ was then applied until the yield point. Stress—strain curves were recorded using TA Universal Analysis 2000 v. 4.5 A software (TA instruments) and the ultimate stress, strain and ultimate stress, and Young's modulus at 2% strain were extrapolated from the graph.

Cell culturing on electrospun (ES)-pcECM scaffolds: Scaffolds were cut into circles (D=0.18 cm), placed in 96-well plates, and sterilized using ultra-violet light. Culture medium was added and plates were then moved into a humidified incubator (37° C., 5% $CO_2$). One hour later, the medium was washed, replaced with a fresh one and the plates were returned to the incubator overnight for wetting. The following day, cells were seeded.

Human bone marrow mesenchymal stem cells (hMSCs, Lonza, Basel, Switzerland) were seeded (10,000 per scaffold) and cultured for 1 month. hMSCs were cultured in αMEM, supplemented with FCS (10%), pen-strep (1%), fungizone (0.4%), and basic fibroblast growth factor (5 ng mL$^{-1}$). The medium was replaced every second day. Cell viability was evaluated using the AlamarBlue™ reagent (AbD Serotec, Kidlington, UK), according to the manufacturer's protocol. hiPSCs were seeded (30,000 per scaffold) and cultured for 1 month. The hiPSCs were cultured in mTeSR Basal Medium and supplemented with mTeSR™ 1 5× supplement. The medium was replaced every day. Neonatal cardiomyocytes were isolated from 24-hr-old Wister rats. Excised hearts were minced, and the cardiac cells were dissociated by gentle agitation in 200 U mL$^{-1}$ RDB in PBS-G (PBS, pen-strep, 0.1% D-glucose) at 37° c for 10 min. Cell suspensions were centrifuged at 1000 rpm for 5 min, suspended in F-10 nutrient mixture supplemented with 5% fetal bovine serum, 5% DHS, 1% pen-strep and 0.4% fungizone and 1 mM $CaCl_2$. Cell suspensions was pre-plated in culture dishes and incubated for 1 hr to allow adherence of the fibroblast cells. The non-attached myocyte-enriched cell suspension was collected, centrifuged as before, and re-suspended in culture medium. Neonatal cardiomyocytes were seeded on scaffolds (200,000 cells/scaffold, n=12) and cultured for 3 weeks in the supplemented F-10 nutrient mixture. The medium was changed every second day.

Lightsheet Fluorescent Microscopy (LSFM): To study the morphology of cells cultured on electrospun ECM scaffolds, cells were stained with FDA (for viable cells), and with Hoechst 33258 (for DNA). Scaffolds were then embedded within low-melting Agarose gel (Bio-Rad, Haifa, Israel) and inserted within a 1 mL syringe. The sample was then observed using light sheet fluorescence microscopy (LSFM) using a Lightsheet Z.1 (Zeiss), equipped with dual sided beam illumination with two aligned objectives for complete, high resolution 3D imaging, two cameras, and a full incubation compartment for live samples.

Histology: Cell-seeded scaffolds were fixed in PFA (4%) for 20 min, washed in PBS and frozen in Tissue-Tek™ OCT compound, cross-sectioned into slices (10 μm) on glass slides and stained. Slides were fixed in cold MeOH (4° C.) for 20 min prior to staining. After fixation, slides were washed in DDW 3-5 times to remove all the OCT compound, and stained with hematoxylin and eosin (H&E). Immunofluorescent staining for cardiac markers was performed using cTn1, sarcomeric alpha-actinin, and connexin-43 primary antibodies, according to the manufacturers' protocol. Slides were visualized by inverted phase-contrast microscopy (Eclipse TE2000-E, Nikon Inc.).

$Ca^{2+}$ imaging: Cells were loaded with 5 mM of fluo-4 fluorescent $Ca^{2+}$ indicator (Molecular Probes) in the presence of Pluronic F-127 (Molecular Probes) at a dilution of 2:1 to allow the recording of intracellular $Ca^{2+}$-transients (whole-cell [$Ca^{2+}$] transients). For pacing, scaffolds were plated on a 35-mm optical plate (Matek) with field simulation electrodes (RC-37FS; Warner Instruments), and paced using a stimulus isolation unit (SIU-102; Warner Instruments), by applying 5 ms-suprathreshold bipolar stimulation pulses up to 50 mA. Intracellular $Ca^{2+}$-transients were recorded using a Zeiss laser-scanning confocal imaging system (Fluo-view; Olympus) mounted on an upright BX51WI Olympus microscope equipped with a X60 water objective. Data were analyzed utilizing MatLab-based custom-written software.

MSCs remodeling of pcECM-based scaffolds: The expression of ECM remodeling-related genes by cells seeded on the pcECM-based scaffolds was quantitatively studied for 21 days, by real-time RT-PCR. The following genes were studied: Collagen I (α1 chain), collagen III (α1 chain), matrix metalloproteinase 2 (MMP2), and type 1 tissue inhibitor of metalloproteinases (TIMP1). Total RNA was isolated from the seeded cells at different time points using Tri-reagent (Sigma-Aldrich) according to the manufacturer's instructions, and reverse-transcribed in a PTC-200 PCR cycler using a Verso™ cDNA kit (Thermo-Scientific). Primers were designed to specifically amplify genes' cDNA as follows:

5'-TACAGCGTCACTGTCGATGGC-3' (SEQ ID NO: 5) and 5'-TCAATCACTGTCTTGCCCCAG-3' (SEQ ID NO: 6) for collagen Iα1.

5'-AATTTGGTGTGGACGTTGGC-3' (SEQ ID NO: 7) and 5'-TTGTCGGTCACTTGCACTGG-3' (SEQ ID NO: 8) for collagen III α1.

5'-TTGACGGTAAGGACGGACTC-3' (SEQ ID NO: 9) and 5'-ACTTGCAGTACTCCCCATCG-3' (SEQ ID NO: 10)for MMP2.

5'-TACTTCCACAGGTCCCACAA-3' (SEQ ID NO: 11) and 5'-ATTCCTCACAGCCAACAGTG-3' (SEQ ID NO: 12) for TIMP1.

5'-CAACAGCGACACCCACTCCT-3' (SEQ ID NO: 13) and 5'-CACCCTGTTGCTGTAGCCAAA-3' (SEQ ID NO: 14) for glyceraldehyde 3-phosphate dehydrogenase (GAPDH) as an intrinsic housekeeping gene control. Reactions were run on the StepOnePlus system, and analyzed using StepOne software v. 2.2.2 (Applied Biosystems).

In vitro immunogenicity assay: Macrophage stimulation was used to evaluate the immunogenicity of the ECM electrospun scaffolds in-vitro. Both levels of secreted nitric oxide (NO) and expression of pro-inflammatory cytokines were measured. RAW cell line (TIB-71™; ATCC Manassas, Va., USA) was seeded in 24-well cell culture plates and cultured in 1 mL high-glucose DMEM supplemented with 10% FCS, 1% Pen-Strep, and 0.4% Fungazone. The following day post seeding, medium was replaced with a low-serum medium (2% FCS). When cells reached 70% confluency, cells were exposed to the following: electrospun ECM scaffolds (1 mg), PLGA as a negative control (1 mg), or LPS as a positive control (1 μg/mL). After a 16 h incubation, secreted NO levels were measured as the free stable nitrite form ($NO_2^-$) in the medium, using the conventional Griess Reagent Assay (reference). Untreated cells also served as a negative control (basal NO secretion). Additionally, total RNA was isolated from the seeded RAW macrophages using Tri-reagent (Sigma Aldrich) according to the manufacturer's protocol, and reverse-transcribed in a PTC-200 PCR cycler using a Verso™ cDNA kit (Thermo-Scientific, Waltham, Mass., USA). The isolated RNA was then used for real-time (RT-) PCR analyses in order to quantify the expression of the pro-inflammatory cytokines TNF-α and IL1-β with the following specific primers.

```
                                            (SEQ ID NO: 1)
    5'-GCCTCCCTCTCATCAGTTCT-3'
    and (SEQ ID NO: 2)
    5'-TGGTGGTTTGCTACGACGTG-3'
    for TNF-α
```

-continued

5'-AGGATGAGGACATGAGCACC-3' (SEQ ID NO: 3)
and

5'-ATGGGAACGTCACACACCAG-3' (SEQ ID NO: 4)
for IL-1β

In vivo immunogenicity study: Immunogenicity experiments were conducted in accordance with the Israeli Animal Welfare (Protection and Experimentation) Law, after obtaining the permission of the Technion's Animal Care Committee. The immunogenic potential of ECM electrospun fibrous scaffolds was additionally evaluated in vivo through subcutaneous implantation. Mice were split into two groups; one group received the electrospun ECM scaffold, and the other received the electrospun PLGA scaffold as a negative control. Each group was split into three time points (1, 2, and 4 weeks). There were five mice per group per time point.

On the day of the surgery, six-week old C57BL mice (Pharma Medis Ltd, Holon, Israel) were anesthetized with a 300 μL peritoneal injection of ketamine (100 mg/kg) (Vetoquinol, Lure, France) and xylasine (5 mg/kg) (Phibro Israel, Beit Shemesh, Israel), shaved on the right flank, and subsequently given 150 μL buprenorphine (0.05 mg/kg) (Vet Market, Shoham, Israel) via subcutaneous injection for pain. During the procedure, an isofluorane/oxygen mixture (2-3% isofluorane) was administered via gas mask for maintenance. Mice were placed on a heating pad (37° C.) and a subcutaneous incision was made on the shaven right flank through which the respective scaffold was inserted. Incisions were stitched and mice were placed into an oxygen-rich, temperature controlled (X ° C.) environment. Mice were routinely monitored, and sacrificed at the respective time points. Blood samples were taken post-mortem from the heart and/or femoral artery for complete blood counts (CBC), inguinal lymph nodes, scaffolds were analyzed. Lymph nodes were homogenized, the mRNA was extracted and reversed transcribed, and proinflammatory cytokines (TNFα and IL-1β levels normalized to GAPDH) were quantified as previously described.

Results

ECM Dissolution and Electrospinning

ECM was obtained from slices of porcine tissues that were decellularized as described in WO 2006095342A2 and in the Materials and methods section herein above, which avoided the use of SDS and allowed for improved preservation of ECM biological activity. ECM were frozen in liquid nitrogen, ground in a cryogenic tissue grinder, and lyophilized. The resulting powder was used for dissolution.

Lyophilized ECM was dissolved in HFIP to a concentration of 0.05 g/mL and pcECM solution was added with 0.1 mass % PEO. Without PEO, pcECM electrospinning resulted in a combination of fibers and spray (FIG. 1A); while with PEO, a network of homogeneous fibers were achieved (FIG. 1B). The PEO was easily removed from the matrix through washes in a water-based medium, and the pcECM fibers remained intact.

Figure 2B:
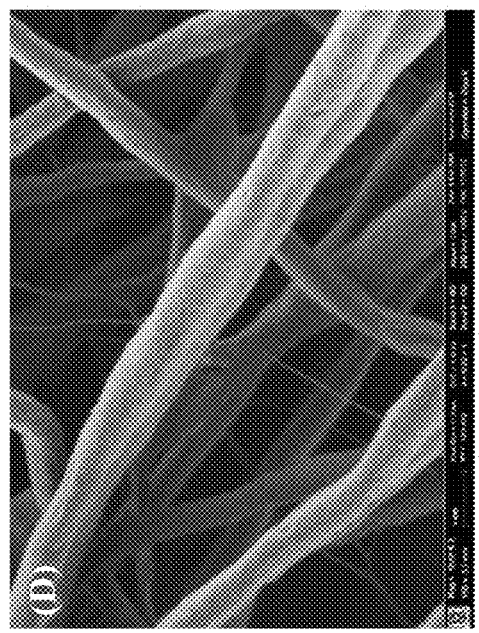
Figure 2C:
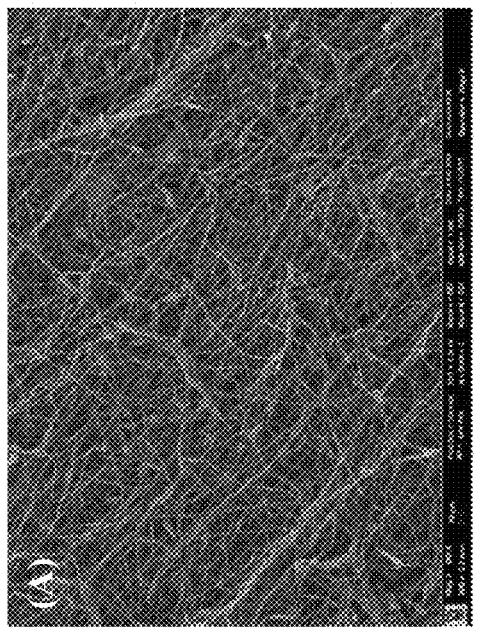
Figure 2D:
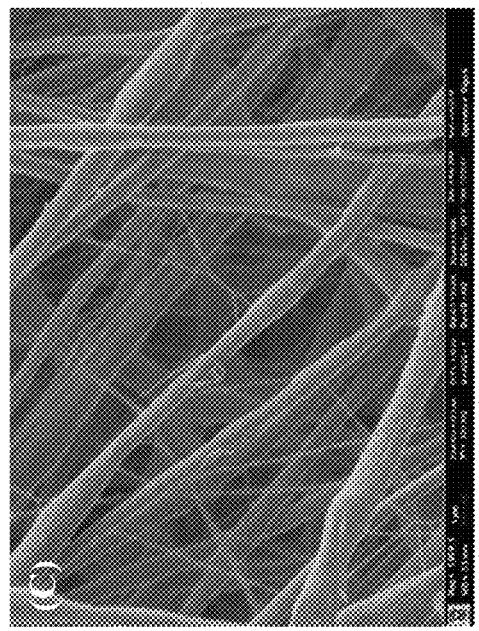
Figure 3B:
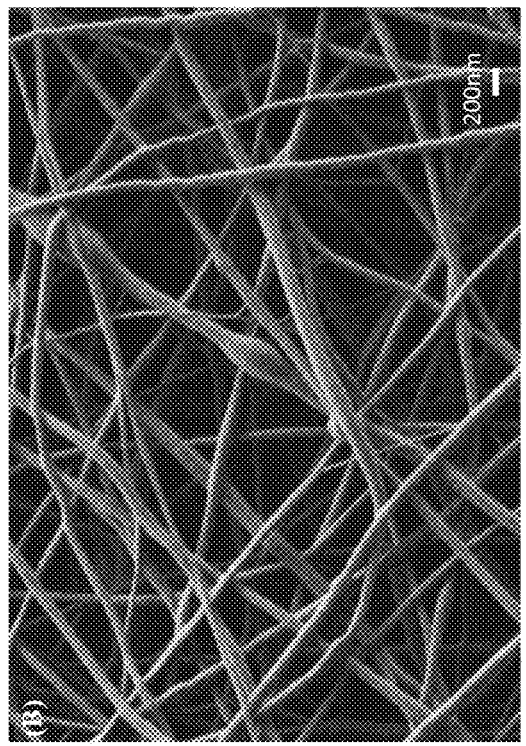
FIGS. 3A-3B are HR-SEM images of porcine pancreas ECM (ppECM) fibers. Scale bars 200 μm.
Figure 3A:
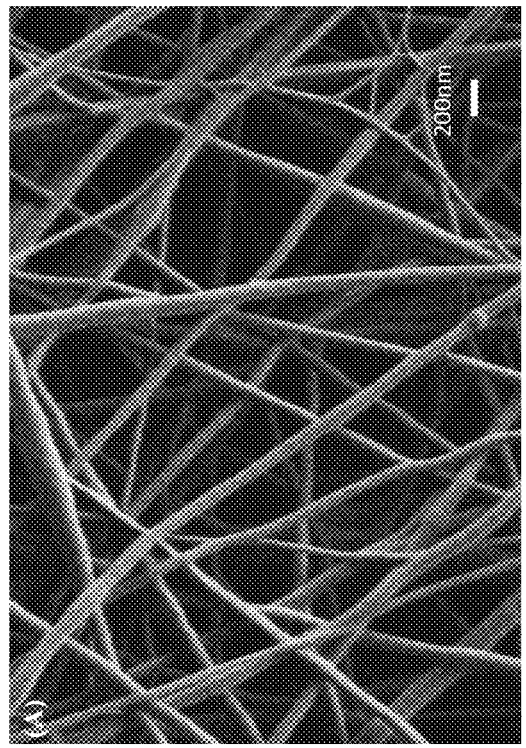
Figure 4:
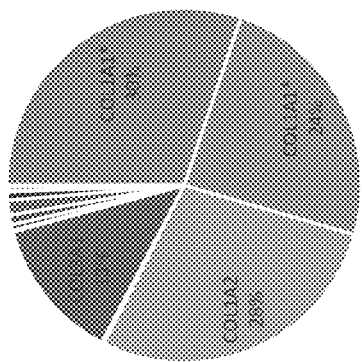
FIG. 4 is a graph illustrating the protein content of pcECM electrospun fibers.
Figure 5:
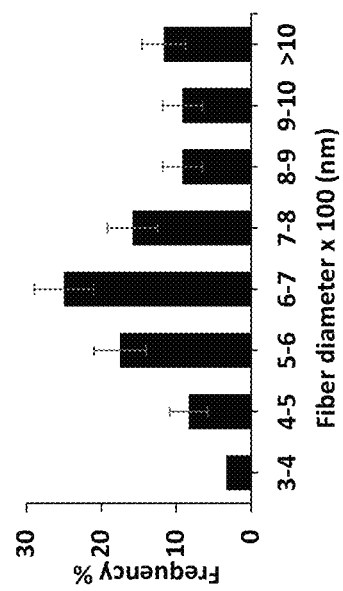
FIG. 5 is a graph illustrating fiber diameter distribution.
Figure 6:
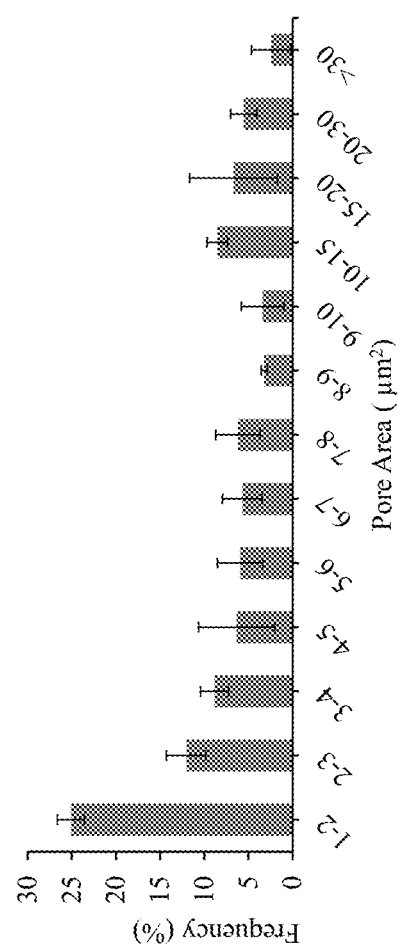
FIG. 6 is a graph illustrating pore size distribution in the electrospun pcECM scaffold.

Scaffold morphology and characterization: HR-SEM images were used to examine the morphology and diameter of the fibers within ECM electrospun fibrous scaffolds (FIGS. 2A-2D, FIGS. 3A-3B). At lower magnifications (0.2-1 kX), the fibers of the electrospun pcECM scaffold appeared randomly dispersed, with minimal non-fiber aggregates, which were suspected to be pieces of collagen that were not fully dissolved (FIGS. 2A-2B). At higher magnitudes (5 kX), two types of fibers were apparent, one quite thick and the other thin. At even higher magnification, (10 kX) the morphology of the porous structure of the individual fibers was visible (FIG. 2D). According to imageJ analyses, the diameter of the larger fibers was approximately 734±228 nm, ranging from 300 to 1500 nm, exhibiting a normal distribution (FIG. 5), consistent with natural ECM.[10] The diameter of the thinner fibers was approximately 43±7.9 nm, which still falls within the range of the fiber diameter seen in natural ECM. Pore size of the electrospun pcECM scaffold ranged between 1-30 μm$^2$, with an average of 7.6±1.7 μm$^2$ (FIG. 6).

Figure 7:
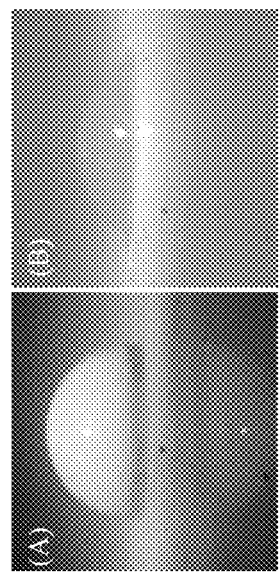
FIGS. 7A-7B are photographs of initial wetting/contact angle of the electrospun pcECM scaffold (A), and the wetting/contact angle after 5 min (B).
Figure 8:
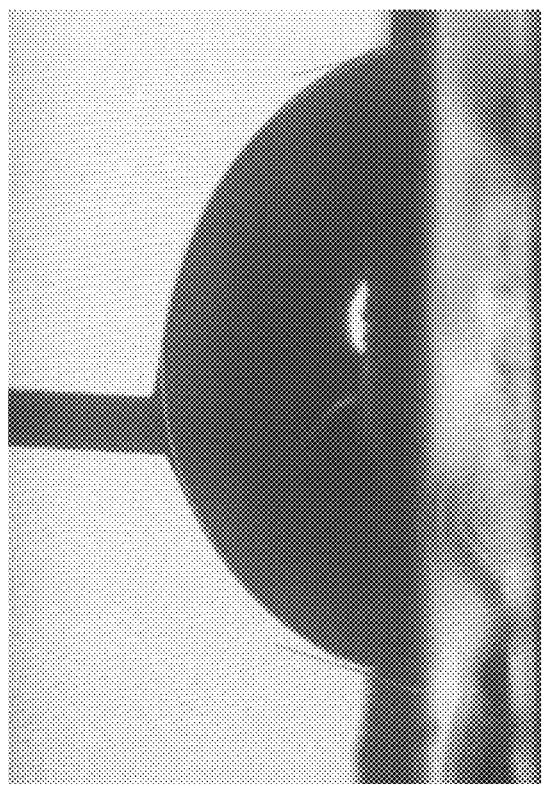
FIG. 8 is a photograph of initial wetting/contact angle of the electrospun ppECM scaffold.

The contact angle of the ECM electrospun fibrous scaffolds was observed by dropping a 1 mm droplet of DDW on the surface, and capturing a static image. Analysis was performed using a home-designed MatLab program. The water contact angle of electrospun pcECM and ppECM scaffolds was 96.33±2.12° or 74.3 respectively. After less than 5 minutes, the contact angle of electrospun pcECM decreased to 60° (FIG. 7A-7B and FIG. 8).

Figures 9A, 9B:
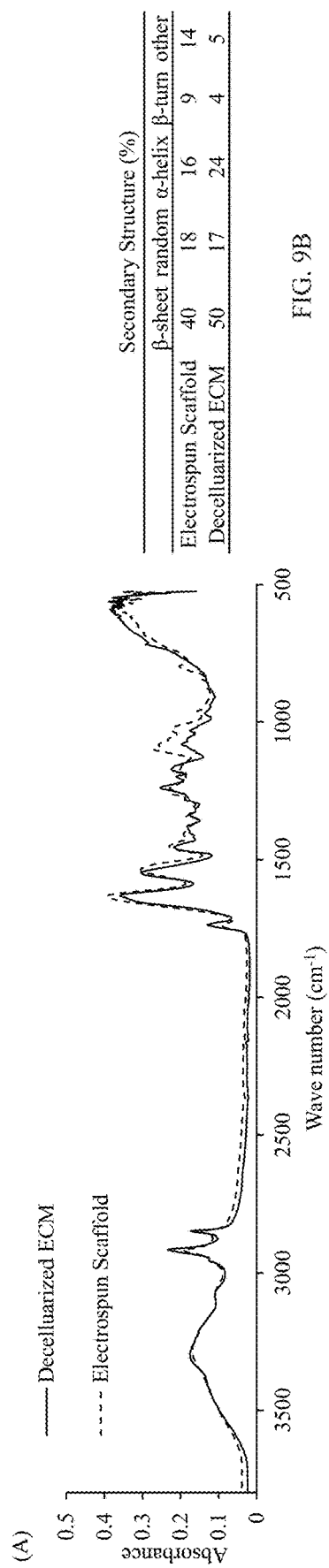
FIGS. 9A-9B are a graph illustrating the Fourier transform infrared spectroscopy (FTIR) spectra of the electrospun pcECM scaffold compared to decellularized pcECM (A), and the secondary structure of scaffold proteins determined by Fourier deconvolution of their amid I band (B).

ECM electrospun fibrous scaffolds composition: Since the protein composition is a major factor contributing to the biological activity and mechanical properties of the scaffold, possible changes in protein composition were first evaluated by comparing FTIR spectra obtained from decellularized pcECM to those of the ES-pcECM scaffold (FIG. 9A-9B). Both materials exhibited amide vibrations, near and above 3000 cm$^{-1}$, characteristic of peptide groups, and vibrations between 500-1700 cm$^{-1}$, characteristic of amino acid side chains, with no significant differences between decellularized pcECM and ES-pcECM scaffold. Moreover, similar percentages of each secondary structure were determined by Fourier deconvolution. Proteomic mass spectrometry analyses were performed to ensure that proteins were not lost during the dissolution or electrospinning process. Since collagen is the most abundant protein in ECM, and provides the necessary tensile strength and viscoelasticity, the collagen content was inspected thoroughly (Table 1, Table 2, and FIG. 3).

TABLE 1

| Accession # | Gene | Level of abundance |
|---|---|---|
| F1SFA7 | Collagen alpha-2(I) | Level 1 |
| F1RYI8 | Collagen alpha-1(III) | Most abundant |
| F1RT61 | Collagen alpha-1(I) | proteins |
| I3LJX2 | similar to collagen alpha-1(I)* | |
| F1RLL9 | (Fragment) Collagen alpha-2(IV) | Level 2 |
| F1S021 | (Fragment) Collagen alpha-1(V) | >3 fold decrease |
| I3LSV6 | (Fragment) Collagen alpha-1(II) | from level 1 |
| Q59IP2 | Procollagen alpha 2(V) | |
| I3LQ84 | Collagen alpha-2(VI)** | Level 3 |
| I3LUR7 | Collagen alpha-3(VI) | >20 fold decrease |
| F1RLM1 | (Fragment) Collagen alpha-1(IV) | from level 1 |
| I3LS72 | Collagen alpha-1(VI) | >3 fold decrease |
| F1S3G7 | (Fragment) Collagen alpha-3(V) | from level 2 |
| F1SKX7 | Collagen alpha-1(VIII) | Level 4 |
| D5KRL1 | Collagen alpha-1(XXI) | >100 fold decrease from level 1 >60 fold decrease from level 2 >8 fold decrease from level 3 |

Table 2 presents the collagenous composition of electrospun porcine pancreatic ECM (ppECM) scaffold as revealed in proteomic analysis.

| Gene Name | Score | Coverage |
|---|---|---|
| COL1A2 | 496.16 | 52.2 |
| COL3A1 | 190.58 | 21.7 |
| COL1A1 | 80.31 | 66.5 |
| COL2A1 | 39.48 | 3.2 |
| COL5A1 | 25.32 | 3.1 |
| COL5A2 | 24.31 | 8.9 |
| COL5A3 | 4.65 | 3.4 |

All collagen types were grouped by their level of abundance as according to their mass spectrometry results; level 1 signifying the most abundant collagen. When a significant fold decrease was detected, the collagen was placed in the subsequent level. For example, all the collagen in level 2 had larger than a 3 fold decrease in their level of abundance from all the collagen in level 1. Level 3 collagen decreased in abundance more than 20 fold from level 1 and 3 fold from level 2, while level 4 collagen decreased more than 100 fold from level 1, 60 fold from level 2, and 8 fold from level 3. These groupings allowed for a more in-depth analysis of the collagen composition of the pcECM electrospun scaffold. Level 1 contains only collagen types I and III, which is expected, since collagen types I and III, usually found together, are the most plentiful collagen within cardiac ECM tissue, (>90%).[15] They are fibril, interstitial collagen types that maintain tissue structure and support cardiomyocytes.

Levels 2 and 3 contain the less abundant fibrillar forming collagens (II and V), and network forming collagen that is present in basement membranes (IV). Level 3 also contains collagen type VI, which provides a microfilament network that organizes the fibrillary collagens and anchors them to the basement membranes. Collagen alpha-2 (VI) was the only collagen that exhibited a significant fold decrease in the pcECM electrospun scaffold from the decellularized pcECM. In general, it was determined that, with the exception of collagen alpha-2 (VI), there was no significant fold difference in the collagen content between the decellularized pcECM and the pcECM electrospun scaffold.

Figure 10:
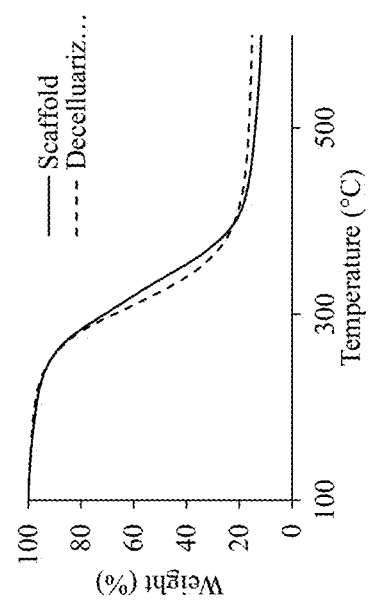
FIG. 10 is a graph illustrating the thermal gravimetric analysis (TGA) curves representing the degradation behavior over temperature of the electrospun pcECM scaffold and decellularized pcECM.
Figures 12A, 12B, 12C, 12D:
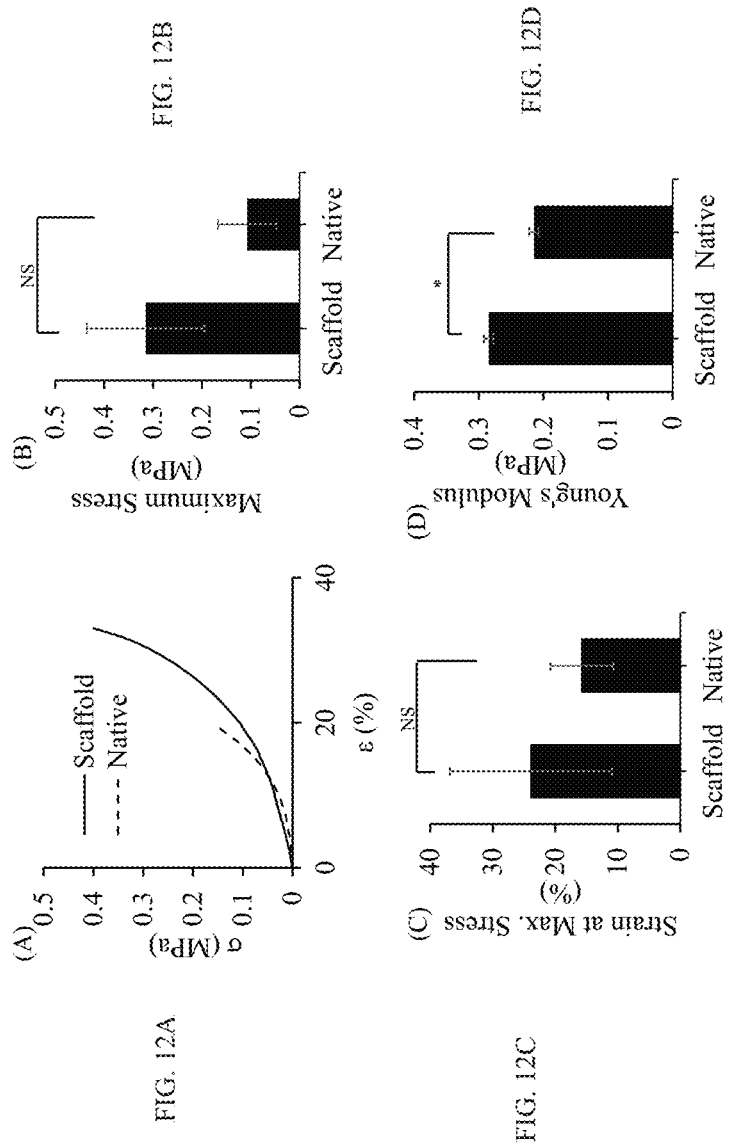
FIGS. 12A-12D are graphs illustrating the mechanical properties of the electrospun pcECM scaffold compared to native tissue in physiological solution, visualized in terms of a stress-strain curve (A), maximum stress (B), strain at maximum stress (C), and Young's Modulus (D).

TGA analyses (FIG. 10), compared the characteristic thermal degradation of the scaffold to that of decellularized pcECM. The onset of decomposition ($T_{onset}$) was similar for both materials: 259.4° C. (scaffold) and 259.6° C. (decellularized pcECM), signifying that the production process of ES-pcECM scaffolds, and particularly the dissolution of pcECM in HFIP, had not degraded the collagen.

Self-assembly of electrospun pcECM: Upon wetting the ES-pcECM scaffold, the electrospun fibers underwent self-assembly, consequently obviating the need for a synthetic cross-linking agent (FIG. 11). The extent of self-assembly varied according to the initial wetting temperature as well as the subsequent incubation temperature. The largest degree of self-assembly was obtained when ES-pcECM scaffolds were maintained at 37° C., where the ES-pcECM self-assembly produced an isotropic, porous, ordered structure that most clearly and uniquely resembled the microstructure of native pcECM. ES-pcECM scaffolds maintained at 24° C. showed a lower degree of self-assembly, and those maintained at 4° C. showed minimal self-assembly, and anisotropic structures with electrospun fibers still very apparent. Increasing the incubation temperature post initial wetting (from 4° C. and 24° C.) to 37° C. increased their self-assembly; however, complete self-assembly was not achieved, and electrospun fibers were still present to some extent. These studies provide a wealth of data regarding the abilities of the ES-pcECM scaffold, which had not been observed with the electrospinning of other natural polymers.

Mechanical properties of the electrospun pcECM scaffold: The mechanical properties of an engineered scaffold are particularly critical when addressing cardiac regeneration. The mechanical properties of the electrospun pcECM scaffold were compared to those of native tissue in a physiological solution (FIG. 12A-12D). The stress and strain at maximum stress were similar in the electrospun pcECM scaffold and native cardiac tissue (p>0.05). The Young's modulus (E) of the scaffolds (0.29±0.007 MPa) was also comparable to that of native tissue (0.22±0.007), though statistically different (p<0.05). Such findings confirmed that self-assembly of electrospun pcECM scaffold is sufficient to obtain the mechanical properties desired for cardiac regeneration with no need for a synthetic cross-linking agent.

Figure 13:
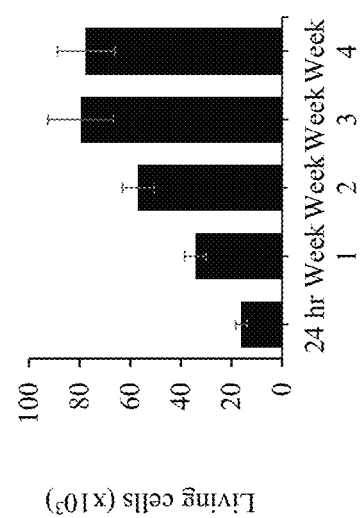
FIG. 13 is a graph illustrating the viability of hMSCs on pcECM electrospun fibrous scaffolds after 24 h and 1 to 4 weeks.
Figures 15A, 15B, 15C:
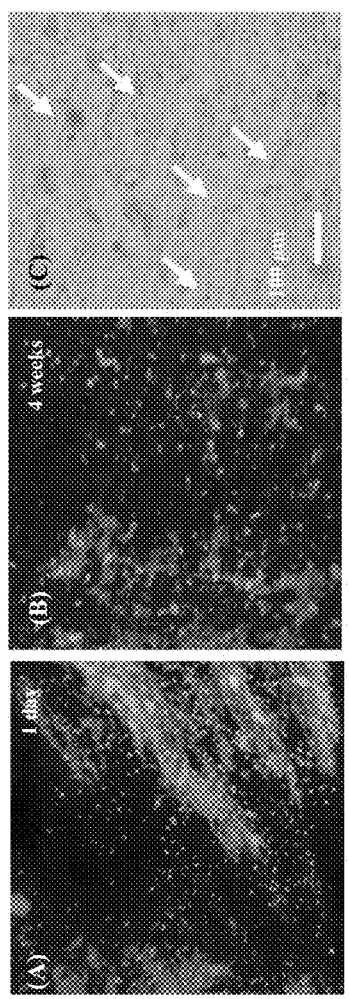
FIGS. 15A-15C are images of hMSCs on pcECM electrospun fibrous scaffolds. Light sheet fluorescent microscopy (LSFM) images at 1 day (A) and 4 weeks (B) using Hoechst 33258 (DNA-blue), while observing the ECM autofluorescence (red and green). Hematoxylin and eosin (H&E) staining at 4 weeks post seeding (C).
Figures 16A, 16B, 16C, 16D:
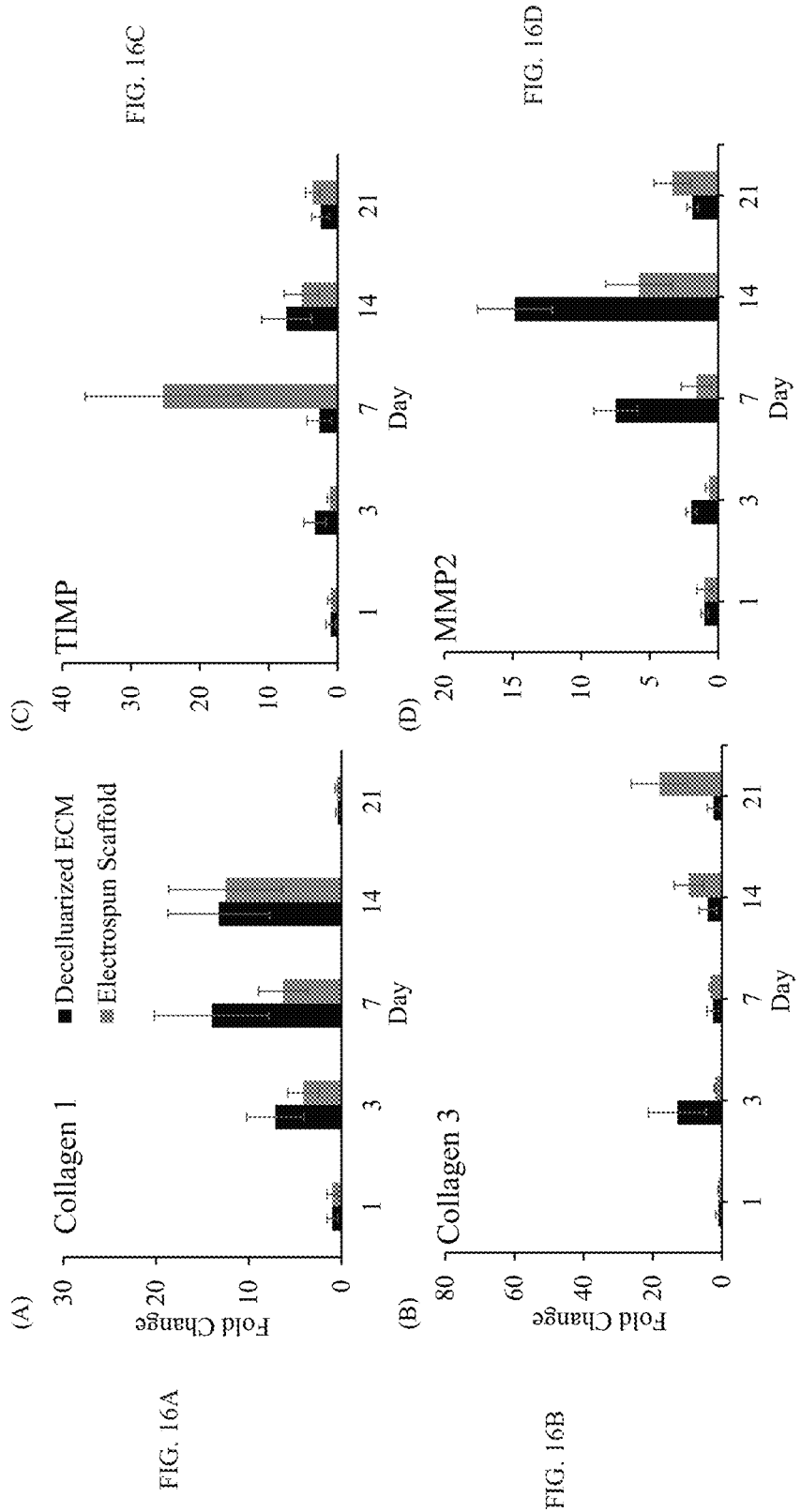
FIGS. 16A-16D are graphs illustrating the relative expressions of ECM remodeling genes by hMSCs grown on the electrospun pcECM scaffold compared to native pcECM. Collagen I (A) Collagen III (B) Tissue inhibitor of metalloproteinases type 1 (TIMP1) (C) Matrix metalloproteinase-2 (MMP2) (D).
Figure 17:
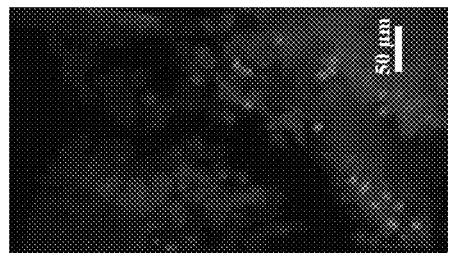
FIG. 17 is a LSFM image of electrospun pcECM scaffold seeded with human induced pluripotent stem cells (hiPSCs) at 3 weeks post seeding.

Culturing hMSCs on pcECM electrospun fibrous scaffolds: The ability for cells to adhere to and proliferate on the pcECM electrospun fibrous scaffold was assessed in terms of the viability of human mesenchymal stem cells (hMSCs). Viability studies confirmed that the pcECM electrospun scaffold supported the hMSCs, which remained at an average density of 80,000 cells per scaffold for up to 4 weeks (FIG. 13).

hMSCs portrayed normal elongated morphology and scaffold penetration (FIGS. 14A-14D). The presence of adherent, viable hMSCs after 1 month of culture on the scaffold was also supported by light sheet fluorescence microscopy (LSFM) analysis (FIGS. 15A-15B). Hematoxylin and eosin (H&E) histological analysis demonstrated that the cells had integrated within the matrix (FIG. 15C).

The seeded hMSCs' ability to remodel the electrospun pcECM scaffold was evaluated by analyzing their expression of ECM-remodeling related genes (FIG. 16A-16D). In both native ECM and the electrospun ECM scaffold, collagen I expression increased 3, 7, and 14 days post seeding in 10-20 folds compare to the basal level. This elevated expression decreased by day 21. Maximal increase of collagen III expression was observed in day 3 for the native ECM (13 fold) and day 21 for the electrospun ECM scaffold (18 fold). TIMP1 (collagenase inhibitor), maximal expression was observed at day 7 for the electrospun scaffold (25 fold) and day 14 for the native ECM (7 fold). MMP2, an indicator collagenase, increased at day 7, and reached maximal expression at day 14 on both native ECM and the electrospun ECM scaffold.

Figure 18B:
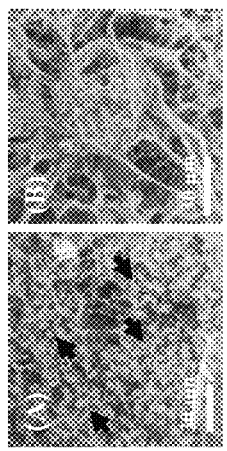
FIGS. 18A-18D are images of hiPSCs cultured on pcECM electrospun fibrous scaffolds. SEM images (A-C) and H&E staining (D) at 3 weeks post seeding.
Figure 18D:
Figure 18A:
Figure 18C:
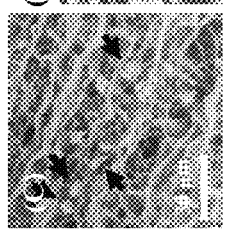

Human induced pluripotent stem cells (hiPSC) were seeded on electrospun ECM scaffolds, exhibiting a confluent matrix after three weeks in culture (FIG. 17), with impressive viability levels demonstrated through the small portion of dead cells (propidium iodide, pink). CryoSEM images revealed adherent hiPSCs in their regular cluster morphology (FIG. 18A-18C), and H&E analysis showed their integration within the matrix (FIG. 18D).

Figures 19A, 19B, 19C:
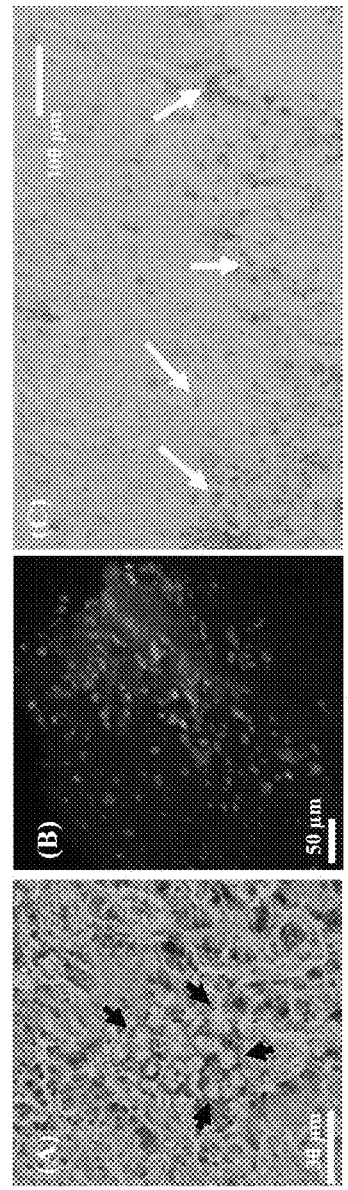
FIGS. 19A-19C are images of cardiomyocytes cultured on pcECM electrospun fibrous scaffolds. SEM image (A) LSFM image (B) and H&E staining (C) at 3 weeks post seeding.
Figure 21:
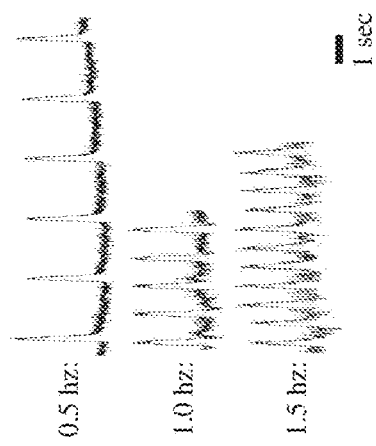
FIG. 21 is a confocal line scan images showing changes in intracellular $Ca^{2+}$ in a Fluo-4 loaded neonatal cardiomyocytes seeded electrospun (ES)-pcECM scaffold 2 weeks post seeding. Whole cell $Ca^{2+}$ transient in three different induced pacing frequencies are shown.

Neonatal rat cardiomyocytes (rCM) seeded on the electrospun pcECM scaffolds were assessed after 21 days using SEM and LSFM (FIGS. 19A-19B), and revealed normal spherical morphology. H&E staining demonstrated the cells' integration within the matrix (FIG. 19C). The seeded rCM were positively stained for the typical functional cardiac proteins cardiac troponin I (cTn1), sarcomeric alpha-actinin and connexin-43 (FIG. 20A-20C), indicating contractile functioning as well as cell-cell coupling through functional gap junctions. This contractile function was also demonstrated through the spontaneous beating of the seeded scaffolds, initiated less than 2 days post seeding. After approximately two weeks, the synchronically beating scaffold was analyzed using $Ca^{2+}$ imaging to record beating and to test electrical coupling. The action potential properties evaluated during pacing (using field stimuli) at different rates (FIG. 21) further confirmed that the electrospun pcECM scaffold can support the cells' intact synchronized electrical activity.

Figure 22:
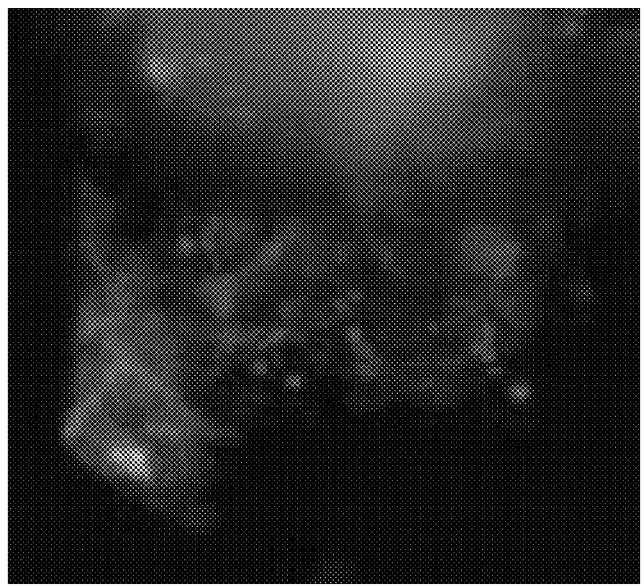
FIG. 22 is a LSFM image of electrospun pcECM scaffold seeded with hiPSCs that were differentiated into cardiomyocytes (hiPSC-CM) at 3 weeks post seeding. green: phalloidin—FITC (Actin), blue: Hoechst (DNA).
Figure 23:
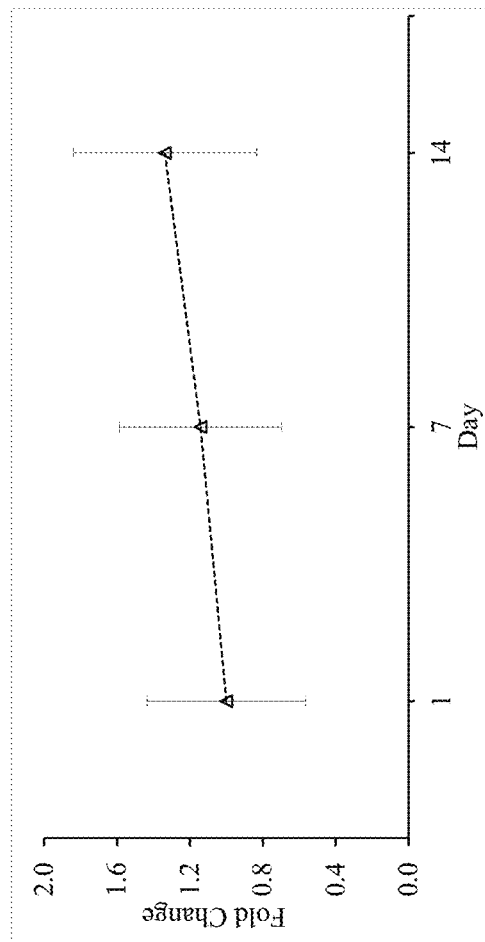
FIG. 23 is a graph illustrating the viability of hiPSC-CMs on pcECM electrospun scaffolds after 1, 7 and 14 days.
Figure 24:
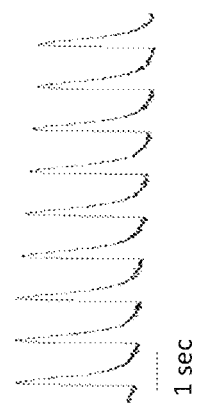
FIG. 24 is a confocal line scan images showing changes in intracellular $Ca^{2+}$ in a Fluo-4 loaded hiPSC-CM seeded electrospun pcECM scaffold 14 days post seeding. Whole cell $Ca^{2+}$ transient in 1 Hz induced pacing frequency are shown.

The cultivation of an additional type of cells—hiPSC-derived cardiomyocytes (hiPSC-CM)—on electrospun pcECM scaffold revealed high viability levels 14 days and 3 weeks post seeding (FIGS. 22, FIG. 23). Contractile function was also demonstrated through the spontaneous beating of the seeded scaffolds, initiated less than 24 hr post seeding. After approximately two weeks, the synchronically beating scaffolds was analyzed using $Ca^{2+}$ imaging to test electrical coupling. As seen in FIG. 24, whole-cell $[Ca^{2+}]$ transients during pacing (using field stimuli) at 1 Hz rates was achieved, displaying as a line-scan tracing and further confirming that the electrospun pcECM scaffold can support the cells' intact synchronized electrical activity.

Immunogenicity Studies

Immunogenicity of pcECM electrospun scaffolds was examined both in vitro and in vivo. RAW macrophages were stimulated with crushed pcECM scaffolds, PLGA (negative control), lipopolysaccharide (LPS-positive control). Non-stimulated cells were also used as a negative control. After a 16 h incubation period with the stimulated materials, the level of secreted nitric oxide (NO) was evaluated (FIG. 25A). There was no significant change observed in the level of secreted NO between the pcECM scaffolds, PLGA, and non-stimulated cells ($P>0.05$). However, the level of secreted NO was significantly higher ($P<0.01$) for cells stimulated with LPS as compared to pcECM scaffolds and both negative controls, which demonstrated that LPS was a successful positive control. Pro-inflammatory cytokine expression of TNF-α and IL1-β for the RAW macrophages were also evaluated 16 h post stimulation with real-time (RT-) PCR analysis (FIGS. 25B, C). Similar results to the NO excretion were obtained. The expression of the pro-inflammatory cytokine TNF-α showed a 1.66±0.64 fold increase for RAW macrophages stimulated with pcECM scaffolds, while there exhibited at 0.73±0.65- and a 67.5±32.6-fold increase for RAW macrophages stimulated with PLGA and LPS, respectively (with respect to non-stimulated cells). Only the fold increase of the TNF-α expression exhibited by RAW macrophages stimulated with LPS can be considered highly significant ($P<0.01$). The expression of the pro-inflammatory cytokine IL1-β showed a 2.69±1.79 fold increase for RAW macrophages stimulated with pcECM scaffolds, while there exhibited at 0.25±0.26- fold and a 18,124±14,581-fold increase for RAW macrophages stimulated with PLGA and LPS, respectively (with respect to non-stimulated cells). Only the fold increase of the IL1-β expression exhibited by RAW macrophages stimulated with LPS can be considered highly significant ($P<0.01$).

The immunogenicity of pcECM electrospun fibrous scaffolds was additionally evaluated in vivo through subcutaneous implantation. Mice were split into two groups; one group received the pcECM scaffold, and the other received electrospun PLGA scaffolds as a negative control. One, two and four weeks following implantation the mice were sacrificed. Lymph node examination revealed no swelling or irritation in all tested groups. In addition, the expression of pro-inflammatory cytokines TNF-α and IL1-β in the lymph nodes revealed no significant difference between the ES-pcECM scaffold groups and the ES-PLGA scaffold groups of the same week (FIGS. 26A-26B). Complete blood counts (CBC) revealed no increase in the levels of white blood cells (WBCs), red blood cells (RBCs), hematocrit, hemoglobin, mean corpuscular volume (MCV), mean corpuscular hemoglobin (MCH), MCH concentration (MCHC), neutrophils, and lymphocytes at the ES-pcECM scaffold treatment group compared to the PLGA negative control group for all time points (FIG. 27A-27I).

Overall, these immunogenicity studies demonstrated that pcECM electrospun fibrous scaffolds, although taken from a porcine source and solubilized in a hazardous organic solvent, are non-immunogenic. Thus, they are candidates for use a biocompatible cardiac scaffolds, for repairing damaged tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Badylak, S. E. The extracellular matrix as a scaffold for tissue reconstruction. *Seminars in Cell & Developmental Biology* 13, 377-383 (2002).
2. Uriel, S. et al. Extraction and assembly of tissue-derived gels for cell culture and tissue engineering. *Tissue Engineering Part C: Methods* 15, 309-321 (2008).
3. Ghorani, B. & Tucker, N. Fundamentals of electrospinning as a novel delivery vehicle for bioactive compounds in food nanotechnology. *Food Hydrocolloids* 51, 227-240 (2015).
4. Yu, J. H., Fridrikh, S. V. & Rutledge, G. C. The role of elasticity in the formation of electrospun fibers. *Polymer* 47, 4789-4797 (2006).
5. Dong, B., Arnoult, O., Smith, M. E. & Wnek, G. E. Electrospinning of Collagen Nanofiber Scaffolds from Benign Solvents. *Macromolecular Rapid Communications* 30, 539-542 (2009).
6. Punnoose, A. M., Elamparithi, A. & Kuruvilla, S. Electrospun Type 1 Collagen Matrices Using a Novel Benign Solvent for Cardiac Tissue Engineering. *J Cell Physiol* (2015).
7. Nieuwland, M. et al. Food-grade electrospinning of proteins. *Innovative Food Science & Emerging Technologies* 20, 269-275 (2013).
8. Burck, J. et al. Resemblance of electrospun collagen nanofibers to their native structure. *Langmuir: the ACS journal of surfaces and colloids* 29, 1562-1572 (2013).
9. Heydarkhan-Hagvall, S. et al. Three-dimensional electrospun ECM-based hybrid scaffolds for cardiovascular tissue engineering. *Biomaterials* 29, 2907-2914 (2008).

10. Barnes, C. P., Sell, S. A., Boland, E. D., Simpson, D. G. & Bowlin, G. L. Nanofiber technology: Designing the next generation of tissue engineering scaffolds. *Advanced Drug Delivery Reviews* 59, 1413-1433 (2007).
11. Jugdutt, B. I. Remodeling of the myocardium and potential targets in the collagen degradation and synthesis pathways. *Current Drug Targets—Cardiovascular & Haematological Disorders* 3, 1-30 (2003).
12. Gibson, M. et al. Tissue Extracellular Matrix Nanoparticle Presentation in Electrospun Nanofibers. *Biomed Research International* (2014).
13. Sethuraman, A., Han, M., Kane, R. S. & Belfort, G. Effect of surface wettability on the adhesion of proteins. *Langmuir* 20, 7779-7788 (2004).
14. Kitsara, M. et al. Fabrication of cardiac patch by using electrospun collagen fibers. *Microelectronic Engineering* 144, 46-50 (2015).
15. Corda, S., Samuel, J. L. & Rappaport, L. Extracellular matrix and growth factors during heart growth. *Heart failure reviews* 5, 119-130 (2000).
16. Kwak, H.-B. Aging, exercise, and extracellular matrix in the heart. *Journal of exercise rehabilitation* 9, 338-347 (2013).
17. Luther, D. J. et al. Absence of Type VI Collagen Paradoxically Improves Cardiac Function, Structure, and Remodeling After Myocardial Infarction. *Circulation Research* 110, 851-U125 (2012).
18. Silva, G. V. et al. Mesenchymal stem cells differentiate into an endothelial phenotype, enhance vascular density, and improve heart function in a canine chronic ischemia model. *Circulation* 111, 150-156 (2005).
19. Fukuda, K. Development of regenerative cardiomyocytes from mesenchymal stem cells for cardiovascular tissue engineering. *Artificial organs* 25, 187-193 (2001).
20. McAnulty, R.J. Fibroblasts and myofibroblasts: their source, function and role in disease. *The international journal of biochemistry & cell biology* 39, 666-671 (2007).
21. Eitan, Y., Sarig, U., Dahan, N. & Machluf, M. Acellular cardiac extracellular matrix as a scaffold for tissue engineering: in vitro cell support, remodeling, and biocompatibility. *Tissue Eng Part C Methods* 16, 671-683 (2010).

What is claimed is:

1. A method of generating a scaffold comprising:
   (a) homogenizing decellularized extracellular matrix (ECM) in an organic solvent using a bead homogenizer to generate a homogenate of decellularized ECM;
   (b) contacting said homogenate of decellularized ECM with a synthetic polymer so as to increase viscoelasticity of said homogenate of decellularized ECM, wherein an amount of said synthetic polymer in said homogenate of decellularized ECM is between 0.05-1% mass of said homogenate of decellularized ECM; and subsequently
   (c) electrospinning said homogenate of decellularized ECM onto a solid surface thereby generating the scaffold composed of ECM fibers; and subsequently
   (d) removing said polymer following said electrospinning such that the scaffold is devoid of said synthetic polymer, wherein the method is performed in-vitro.

2. The method of claim 1, wherein said ECM is not derived from fat tissue.

3. The method of claim 1, wherein said ECM is derived from an organ selected from the group consisting of heart and pancreas.

4. The method of claim 1, further comprising decellularizing a tissue of a subject to generate said decellularized ECM prior to step (a).

5. The method of claim 1, wherein said homogenizing is effected at 6000 rpm.

6. The method of claim 1, wherein said organic solvent is selected from the group consisting of acetone, N,N-dimethylformamide (DMF), diethylformamide, chloroform, methylethylketone, acetic acid, formic acid, ethanol, 1,1,1,3,3,3-hexa fluoro-2-propanol (HFIP), tetrafluoroethanol, dichloromethane (DCM), tetrahydrofuran (THF), trifluoroacetic acid (TFA), camphorsulfonic acid, dimethyl acetamide, isopropyl alcohol (IPA) and mixtures thereof.

7. The method of claim 1, wherein said organic solvent is HFIP.

8. The method of claim 1, wherein said synthetic polymer is selected from the group consisting of poly(D,L-lactide) (PLA), poly(urethanes), poly(siloxanes), poly(silicones), poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), polyorthoesters and mixtures thereof.

9. The method of claim 8, wherein said synthetic polymer is PEO.

10. The method of claim 1, further comprising sonicating said homogenate of decellularized ECM following step (a) and prior to step (b).

11. The method of claim 1, further comprising mixing said homogenate of decellularized ECM by placing on a rotator for at least 1 day prior to step (b).

12. The method of claim 1, further comprising filtering said homogenate of decellularized ECM to remove any particulate matter following step (a) and prior to step (c).

13. The method of claim 1, wherein said removing is by rinsing in an aqueous solution.

\* \* \* \* \*